US00RE50403E

(19) United States
(12) Reissued Patent
Jones et al.

(10) Patent Number: US RE50,403 E
(45) Date of Reissued Patent: *Apr. 29, 2025

(54) SYSTEMS AND METHODS FOR DELIVERING BONE CEMENT TO A BONE ANCHOR

(71) Applicant: DePuy Synthes Products, Inc., Raynham, MA (US)

(72) Inventors: Bryan S. Jones, West Roxbury, MA (US); Michael Michielli, Medway, MA (US); Mark Hall, Bridgewater, MA (US); Kevin Lee, Canton, MA (US)

(73) Assignee: DePuy Synthes Products, Inc., Raynham, MA (US)

( * ) Notice: This patent is subject to a terminal disclaimer.

(21) Appl. No.: 17/567,107

(22) Filed: Dec. 31, 2021

Related U.S. Patent Documents

Reissue of:
(64) Patent No.: 9,265,548
Issued: Feb. 23, 2016
Appl. No.: 13/832,054
Filed: Mar. 15, 2013

U.S. Applications:
(60) Continuation of application No. 16/798,867, filed on Feb. 24, 2020, now Pat. No. Re. 48,870, which is a
(Continued)

(51) Int. Cl.
*A61B 17/88* (2006.01)
*A61B 17/00* (2006.01)
(Continued)

(52) U.S. Cl.
CPC ..... *A61B 17/8805* (2013.01); *A61B 17/7076* (2013.01); *A61B 17/7085* (2013.01);
(Continued)

(58) Field of Classification Search
CPC ..... A61B 17/8805; A61B 17/7076; A61B 17/7085; A61B 17/7098; A61B 17/8816;
(Continued)

(56) References Cited

U.S. PATENT DOCUMENTS 3,987,499 A 10/1976 Scharbach et al.
4,611,681 A 9/1986 Krude
(Continued)

FOREIGN PATENT DOCUMENTS

EP 0340159 1/1993
EP 0340159 B1 1/1993
(Continued)

OTHER PUBLICATIONS

[No Author Listed] "Implants for Surgery—Acrylic Resin Cements", ISO 5833, 2002 (11 pages).
(Continued)

*Primary Examiner* — Catherine S Williams
(74) *Attorney, Agent, or Firm* — Barnes & Thornburg LLP

(57) ABSTRACT

A method of stabilizing a first vertebra and a second vertebra includes implanting a first bone anchor into the first vertebra, implanting a second bone anchor into the second vertebra, connecting a first anchor connection instrument to the first anchor, connecting a second anchor connection instrument the second anchor, positioning a cement delivery tube into a passage provided through the first anchor, delivering bone cement from a bone cement delivery system coupled to the bone cement delivery tube through the passage in the first anchor to the first vertebra, removing the cement delivery tube from the first anchor connection instrument and the first anchor, connecting the cement delivery tube to second anchor connecting instrument connected to the second anchor, delivering bone cement through a passage in the second anchor to the second vertebra, connecting a spinal connection element to the first anchor and the second anchor.

21 Claims, 31 Drawing Sheets

Related U.S. Application Data continuation of application No. 15/238,947, filed on Aug. 17, 2016, now Pat. No. Re. 47,871, which is an application for the reissue of Pat. No. 9,265,548, which is a division of application No. 12/608,333, filed on Oct. 29, 2009, now abandoned.

(60) Provisional application No. 61/109,661, filed on Oct. 30, 2008.

(51) Int. Cl.
*A61B 17/70* (2006.01)
*A61B 17/86* (2006.01)

(52) U.S. Cl.
CPC ..... *A61B 17/7098* (2013.01); *A61B 17/8816* (2013.01); *A61B 2017/0023* (2013.01); *A61B 17/7032* (2013.01); *A61B 17/7086* (2013.01); *A61B 17/864* (2013.01); *A61B 17/8822* (2013.01)

(58) Field of Classification Search
CPC ..... A61B 17/7032; A61B 17/7086; A61B 17/864; A61B 17/8822; A61B 2017/0023
See application file for complete search history.

(56) References Cited

U.S. PATENT DOCUMENTS 4,653,489 A 3/1987 Tronzo
4,950,270 A 8/1990 Bowman
5,019,079 A 5/1991 Ross
5,034,011 A 7/1991 Howland
5,047,030 A 9/1991 Draenert
5,084,050 A 1/1992 Draenert
5,098,435 A 3/1992 Stednitz et al.
5,169,400 A 12/1992 Muhling et al.
5,180,382 A 1/1993 Frigg
5,192,282 A 3/1993 Draenert
5,209,753 A 5/1993 Biedermann
5,435,723 A 7/1995 O'Brien
5,456,685 A 10/1995 Huebner
5,492,442 A 2/1996 Lasner
5,514,137 A 5/1996 Coutts
5,562,672 A 10/1996 Huebner
5,593,410 A 1/1997 Vrespa
5,658,338 A 8/1997 Tullos et al.
5,695,497 A 12/1997 Stahelin
5,697,917 A 12/1997 Sadowski et al.
5,698,497 A 12/1997 Haddon et al.
5,713,903 A 2/1998 Sander
5,725,581 A 3/1998 Brånemark
5,735,898 A 4/1998 Brånemark
5,738,685 A 4/1998 Halm
5,743,912 A 4/1998 Lahille et al.
5,816,812 A 10/1998 Kownacki
5,824,087 A 10/1998 Aspden et al.
5,964,768 A 10/1999 Huebner
5,997,539 A 12/1999 Errico
6,010,508 A 1/2000 Bradley
6,030,162 A 2/2000 Huebner
6,048,343 A 4/2000 Mathis et al.
6,074,393 A 6/2000 Sitoto
6,083,225 A 7/2000 Winslow et al.
6,083,227 A 7/2000 Saurat
6,096,060 A 8/2000 Fitts et al.
6,117,137 A 9/2000 Halm
6,214,012 B1 * 4/2001 Karpman et al. ..... 606/93
6,217,581 B1 4/2001 Tolson
6,267,785 B1 7/2001 Masini
6,283,973 B1 9/2001 Hubbard
6,348,055 B1 2/2002 Preissman
6,355,043 B1 3/2002 Adam
6,375,657 B1 4/2002 Doubler
6,375,659 B1 4/2002 Erbe
6,383,190 B1 5/2002 Preissman
6,402,758 B1 6/2002 Tolson
6,436,100 B1 8/2002 Berger
6,443,988 B2 9/2002 Felt
6,517,542 B1 2/2003 Papay
6,551,323 B2 4/2003 Doubler
6,554,830 B1 4/2003 Chappius
6,565,566 B1 5/2003 Wagner
6,565,572 B2 5/2003 Chappius
6,565,573 B1 5/2003 Ferrante
6,575,976 B2 6/2003 Grafton
6,582,439 B1 6/2003 Sproul
6,585,740 B2 7/2003 Schlapfer
6,589,245 B1 7/2003 Weiler
6,620,169 B1 9/2003 Peterson
6,645,213 B2 11/2003 Sand
6,648,893 B2 11/2003 Dudasik
6,676,664 B1 1/2004 Al-Assir
6,679,890 B2 1/2004 Margulies
6,689,137 B2 2/2004 Reed
6,719,761 B1 4/2004 Reiley
6,752,809 B2 6/2004 Gorek
6,755,829 B1 6/2004 Bono
6,755,835 B2 6/2004 Schultheiss
6,800,078 B2 10/2004 Reed
6,800,079 B2 10/2004 Reed
6,824,564 B2 11/2004 Crozet
6,846,313 B1 1/2005 Rogers
6,863,671 B1 3/2005 Strobel
6,942,666 B2 9/2005 Overaker
6,981,973 B2 1/2006 McKinley
6,981,974 B2 1/2006 Berger
7,097,648 B1 8/2006 Globerman
7,112,205 B2 9/2006 Carrison
7,179,261 B2 2/2007 Sicvol
7,186,255 B2 3/2007 Baynham
7,235,079 B2 6/2007 Jensen
7,250,055 B1 * 7/2007 Vanderwalle ..... 606/92
7,261,716 B2 8/2007 Strobel
7,300,439 B2 11/2007 May
7,309,346 B2 12/2007 Martinek
7,325,470 B2 2/2008 Kay
7,354,442 B2 * 4/2008 Sasso et al. ..... 606/280
7,455,685 B2 11/2008 Justis
7,527,638 B2 5/2009 Anderson
7,544,196 B2 6/2009 Bagga
7,572,263 B2 8/2009 Preissman
7,608,097 B2 10/2009 Kyle
7,621,950 B1 11/2009 Globerman
7,717,947 B1 * 5/2010 Wilberg et al. ..... 606/304
7,766,945 B2 8/2010 Nilsson
7,799,062 B2 9/2010 Crozet
7,824,044 B2 11/2010 Tochigi et al.
7,824,411 B2 11/2010 Varieur
7,824,413 B2 11/2010 Varieur
7,842,044 B2 11/2010 Runco
7,850,717 B2 12/2010 Dewey
7,918,878 B2 4/2011 Songer
7,935,138 B1 5/2011 Richelsoph
8,012,186 B2 9/2011 Pham
8,075,604 B2 12/2011 Denis
8,100,916 B2 1/2012 Kumar et al.
8,147,500 B2 4/2012 Beyar
8,231,632 B1 7/2012 Jordan
8,257,399 B2 9/2012 Biedermann
8,277,494 B2 10/2012 Biedermann
8,308,782 B2 11/2012 Jackson
8,343,201 B2 1/2013 Biyani
8,366,717 B1 2/2013 Jordan
8,372,126 B2 * 2/2013 Trieu et al. ..... 606/304
8,382,811 B2 2/2013 Crook
8,403,973 B2 3/2013 Biyani
8,491,302 B2 7/2013 Arni
8,690,930 B2 4/2014 Biedermann
8,747,411 B2 * 6/2014 Mitchell ..... 606/104
8,758,012 B2 6/2014 Hurson
8,870,836 B2 * 10/2014 Sweeney ..... 604/264
9,265,548 B2 * 2/2016 Jones ..... A61B 17/7098
9,326,801 B2 5/2016 Poulos

(56) References Cited

U.S. PATENT DOCUMENTS

RE47,871 E * 2/2020 Jones ..... A61B 17/7085
RE48,870 E * 1/2022 Jones ..... A61B 17/7085
2001/0004710 A1 6/2001 Felt
2001/0007074 A1 7/2001 Strobel
2001/0021852 A1 9/2001 Chappius
2002/0038123 A1 3/2002 Visotsky
2002/0049447 A1 4/2002 Li
2002/0082605 A1 6/2002 Reiley
2002/0123752 A1 9/2002 Schultheiss
2002/0147454 A1 10/2002 Neto
2002/0169453 A1 11/2002 Berger
2002/0193799 A1 12/2002 Chappuis
2003/0045881 A1 3/2003 Barouk
2003/0045885 A1 3/2003 Margulies
2003/0078589 A1 4/2003 Preissman
2003/0083662 A1 5/2003 Middleton
2003/0105468 A1 6/2003 Gorek
2003/0120277 A1 6/2003 Berger
2003/0130741 A1 7/2003 McMinn et al.
2004/0006346 A1 1/2004 Holmen
2004/0006348 A1 1/2004 Peterson
2004/0015172 A1 1/2004 Biedermann
2004/0092946 A1 5/2004 Bagga
2004/0122431 A1 6/2004 Biedermann
2004/0176767 A1 9/2004 Bickley
2004/0210297 A1 10/2004 Lin
2004/0225292 A1 11/2004 Sasso ..... A61B 17/8811
606/328
2004/0243137 A1 12/2004 Gorek
2004/0260303 A1 12/2004 Carrison
2004/0267265 A1 12/2004 Kyle
2005/0015059 A1 1/2005 Sweeney
2005/0033303 A1 2/2005 Chappuis
2005/0033427 A1 2/2005 Freilich
2005/0038438 A1 2/2005 Anderson
2005/0055026 A1 3/2005 Biedermann
2005/0055030 A1 3/2005 Falahee
2005/0059972 A1 3/2005 Biscup
2005/0065526 A1 3/2005 Drew
2005/0070907 A1 3/2005 Abernathie
2005/0070915 A1 3/2005 Mazzuca
2005/0101961 A1 5/2005 Huebner
2005/0107800 A1 5/2005 Frankel
2005/0131408 A1 6/2005 Sicvol ..... A61B 17/708
606/301
2005/0131421 A1 6/2005 Anderson
2005/0137596 A1 6/2005 Uwaydah
2005/0143823 A1 6/2005 Boyd
2005/0149036 A1* 7/2005 Varieur et al. ..... 606/86
2005/0149053 A1 7/2005 Varieur
2005/0187555 A1 8/2005 Biedermann
2005/0228388 A1 10/2005 Brodke
2005/0228400 A1 10/2005 Chao
2005/0240188 A1 10/2005 Chow
2006/0052794 A1 3/2006 McGill
2006/0074421 A1 4/2006 Bickley
2006/0079905 A1 4/2006 Beyar
2006/0079909 A1 4/2006 Runco
2006/0095040 A1 5/2006 Schlienger
2006/0106390 A1 5/2006 Jensen
2006/0149258 A1 7/2006 Sousa
2006/0149260 A1 7/2006 Lin
2006/0149263 A1 7/2006 Newcomb
2006/0235410 A1 10/2006 Ralph
2006/0264967 A1 11/2006 Ferreyro
2006/0271047 A1 11/2006 Jackson
2006/0271054 A1 11/2006 Sucec
2006/0293692 A1 12/2006 Whipple
2007/0027230 A1 2/2007 Beyar
2007/0032567 A1 2/2007 Beyar
2007/0053765 A1 3/2007 Warnick
2007/0066987 A1 3/2007 Scanlan
2007/0093818 A1 4/2007 Biedermann
2007/0161985 A1 7/2007 Demakas
2007/0233122 A1 10/2007 Denis
2007/0233260 A1 10/2007 Cragg
2007/0248054 A1 10/2007 Chen
2007/0260261 A1 11/2007 Runco
2007/0299450 A1* 12/2007 Her et al. ..... A61B 17/8822
606/279
2008/0020344 A1 1/2008 Hansson
2008/0045956 A1 2/2008 Songer
2008/0065083 A1 3/2008 Truckai
2008/0132956 A1 6/2008 Biedermann
2008/0132957 A1 6/2008 Matthis
2008/0140132 A1 6/2008 Perez-Cruet
2008/0140136 A1 6/2008 Jackson
2008/0147128 A1* 6/2008 Fritzinger ..... 606/304
2008/0154314 A1 6/2008 McDevitt
2008/0154315 A1 6/2008 Jackson
2008/0161864 A1 7/2008 Beck
2008/0177331 A1 7/2008 Perez-Cruet
2008/0177335 A1 7/2008 Melkent
2008/0188898 A1 8/2008 Jackson
2008/0200915 A1 8/2008 Globerman
2008/0212405 A1 9/2008 Globerman
2008/0221623 A1 9/2008 Gooch
2008/0221624 A1 9/2008 Gooch
2008/0228192 A1 9/2008 Beyar
2008/0234744 A1 9/2008 Zylber
2008/0234756 A1 9/2008 Sutcliffe
2008/0234761 A1 9/2008 Jackson
2008/0249530 A1 10/2008 Truckai
2008/0287994 A1 11/2008 Perez-Cruet
2008/0300639 A1 12/2008 Martin
2009/0062868 A1 3/2009 Casutt
2009/0131867 A1 5/2009 Liu
2009/0138044 A1 5/2009 Bergeron et al.
2009/0163956 A1 6/2009 Biedermann
2009/0198291 A1 8/2009 Foley
2009/0248088 A1 10/2009 Biedermann
2009/0264892 A1 10/2009 Beyar
2009/0264895 A1* 10/2009 Gasperut ..... A61B 17/864
606/104
2009/0264942 A1 10/2009 Beyar
2010/0004692 A1 1/2010 Biedermann
2010/0023017 A1 1/2010 Beyar
2010/0030135 A1 2/2010 Mitchell
2010/0076503 A1 3/2010 Beyar
2010/0094352 A1 4/2010 Iott
2010/0114174 A1 5/2010 Jones
2010/0137918 A1 6/2010 Wilcox
2010/0152785 A1 6/2010 Forton
2010/0234904 A1 9/2010 Richelsoph
2010/0256681 A1 10/2010 Hammer
2010/0274295 A1 10/2010 Carls
2010/0318136 A1 12/2010 Jackson
2011/0093021 A1 4/2011 Fanger
2011/0125199 A1 5/2011 Griffin
2011/0125265 A1 5/2011 Bagga
2011/0137355 A1 6/2011 Rinner
2011/0152948 A1 6/2011 Crook
2011/0257690 A1 10/2011 Rezach
2011/0288599 A1 11/2011 Michielli
2012/0130433 A1 5/2012 Huebner
2012/0226285 A1 9/2012 Beyar
2013/0053901 A1 2/2013 Cormier
2013/0085536 A1 4/2013 Biedermann
2013/0204263 A1 8/2013 Jones
2013/0211468 A1 8/2013 Huebner
2014/0148866 A1 5/2014 Globerman
2014/0257410 A1* 9/2014 Biedermann ..... A61B 17/8811
606/304

FOREIGN PATENT DOCUMENTS

EP 716832 11/1995
EP 0716832 A1 6/1996
EP 14055607 4/2004
EP 1430846 6/2004
EP 1491156 12/2004
EP 1430846 B1 8/2006
EP 1769777 4/2007
EP 1769777 A1 4/2007

(56) References Cited

FOREIGN PATENT DOCUMENTS

| | | | |
|---|---|---|---|
| EP | 1491156 | B1 | 12/2008 |
| EP | 1991145 | | 9/2010 |
| EP | 1991145 | B1 | 9/2010 |
| EP | 1405607 | | 10/2013 |
| EP | 1405607 | B1 | 10/2013 |
| FR | 2820630 | | 8/2002 |
| FR | 2820630 | A1 | 8/2002 |
| JP | 7222752 | | 8/1995 |
| JP | H07222752 | A | 8/1995 |
| JP | 2004208790 | A | 7/2004 |
| JP | 2004-208790 | | 7/2007 |
| WO | 1998048738 | A1 | 11/1998 |
| WO | WO 9848738 | | 11/1998 |
| WO | 2001026568 | A1 | 4/2001 |
| WO | 2004032774 | A1 | 4/2004 |
| WO | WO 2004032774 | | 4/2004 |
| WO | 2004100808 | A1 | 11/2004 |
| WO | WO 2004100808 | | 11/2004 |
| WO | 2005058141 | A2 | 6/2005 |
| WO | WO 2005058141 | | 6/2005 |
| WO | 2005087120 | A1 | 9/2005 |
| WO | WO 2005087120 | | 9/2005 |
| WO | 2006070961 | A2 | 7/2006 |
| WO | WO 2006070961 | | 7/2006 |
| WO | 2007036815 | A2 | 4/2007 |
| WO | WO 2007036815 | | 4/2007 |
| WO | 2007122608 | A2 | 11/2007 |
| WO | WO 2007122608 | | 11/2007 |
| WO | 2008124533 | A1 | 10/2008 |
| WO | WO 2008124533 | | 10/2008 |
| WO | WO 2009015100 | | 1/2009 |
| WO | WO-2009015100 | A2 * | 1/2009 ..... A61B 17/70 |
| WO | 2010051386 | A1 | 5/2010 |

OTHER PUBLICATIONS

Brief Communication—Letter from the Opponent to EP Patent No. 2745789, EP Application No. 14157828.6, dated Sep. 6, 2019 (20 pages).

Confidence Surgical Technique Guide Spinal Cement System, 2008, 16 pages.

European Patent Office Opposition Division, Decision Revoking the European Patent No. 2 745 789, EP Application No. 14157828.6, dated Mar. 9, 2020 (19 Pages).

He, Z et al., "Bone cements for percutaneous vertebroplasty and balloon kyphoplasty: Current status and future developments," Journal of Orthopaedic Translation, vol. 3, pp. 1-11, 2015 (11 pages).

Notice of Opposition to EP Patent No. 2745789, EP Application No. 14157828.6, filed Jan. 19, 2018, by Medacta International SA (25 pages).

Summons to Oral Proceedings and Preliminary Opinion of EP re: Opposition procedings in EP Application No. 14157828.6, dated Oct. 16, 2018 (6 pages).

U.S. Appl. No. 61/109,661, filed Oct. 30, 2008 (37 pages).

Decision revoking the European Patent for Application No. EP 14157828.6 dated Apr. 18, 2024 (78 pages).

Confidence Spinal Cement System Brochure, 2008, 6 pages.

Confidence Surgical Technique Guide Spinal Cement System.

* cited by examiner

SYSTEMS AND METHODS FOR DELIVERING BONE CEMENT TO A BONE ANCHOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

*More than one reissue application has been filed for the reissue of U.S. Pat. No. 9,265,548, issued Feb. 23, 2016. This application is a continuation reissue of U.S. application Ser. No. 16/798,867, filed Feb. 24, 2020. U.S. application Ser. No. 16/798,867 is a continuation reissue of U.S. application Ser. No. 15/238,947, filed Aug. 17, 2016, now U.S. Pat. No. RE47,871.* This application *is also a broadening reissue of U.S. Pat. No. 9,265,548, which issued from U.S. application Ser. No. 13/832,054, filed Mar. 15, 2013. U.S. application Ser. No. 13/832,054* is a divisional of U.S. patent application Ser. No. 12/608,333, filed Oct. 29, 2009 (*now abandoned*), which claims priority to U.S. Provisional Patent Application No. 61/109,661, filed Oct. 30, 2008. Each of the aforementioned patent applications is incorporated herein by reference.

BACKGROUND

Bone anchors may be used in orthopedic surgery to temporarily fix bone during the healing or fusion process. One problem with the use of bone anchors is that bone anchors may pullout or otherwise be displaced from the bone prior to the healing or fusion process completing. This problem is particularly common when a bone anchor is positioned in poor quality bone such as osteoporotic bone. Accordingly, there is need for improved instruments and techniques for securing bone anchors to bone that minimize instances of anchor pull out.

SUMMARY

Disclosed herein are systems and methods for delivering bone cement or other materials to one or more bone anchors, such as one or more spinal anchors. In accordance with one aspect, an instrument system for delivering bone cement to a bone anchor may comprise an anchor connection instrument for releasably connecting to a proximal end of the bone anchor. The anchor connection instrument may include a first member coupled to an opposed second member. The first member and/or the second member may have a distal end configured to releasably connect to the proximal end of the bone anchor. The first member is movable between a release position to facilitate release of the anchor connection instrument from the proximal end of the bone anchor and a connect position in which at least one of the first member and the second member is connected to the proximal end of the bone anchor. The first member and the second member define a passage therebetween. The system includes a cement delivery tube positionable in the passage between the first member and the second member of the anchor connection instrument and a bone cement delivery system coupled to the tube.

In accordance with another aspect, a bone anchor system may include a plurality of bone anchors, each of the plurality of bone anchors including a proximal end, a distal bone engaging end, a passage extending from an opening at the proximal end to the distal bone engaging end, and an opening in a sidewall of the distal bone engaging end that communicates with the passage. The bone anchor system may include a bone cement delivery system and a tube connectable to the bone cement delivery system, the tube being sized to fit within the passage of each of the plurality of bone anchors. The bone anchor system may include an anchor connection instrument for releasably connecting to a proximal end of one of the plurality of bone anchors, the anchor connecting instrument including a first member pivotally coupled to an opposed second member. At least one of the first member and the second member may have a distal end configured to releasably connect to an exterior of the proximal end of one of the bone anchors. The first member and the second member may be pivotable between a spaced apart first position to facilitate release of the anchor connection instrument from the proximal end of one of the bone anchors and a second position in which the first member and the second member connect to the proximal end of one of the plurality of bone anchors. The bone anchor system may include a tube connector positionable within a passage provided between the first member and the second member of the anchor connecting mechanism for connecting the tube to the anchor connection instrument. The tube connector may have an opening sized to receive the tube therethrough that may be sized to permit the tube to move along a longitudinal axis of the tube and may be sized to restrict motion of the tube in a direction transverse to the tube.

In accordance with another aspect, a method of stabilizing a first vertebra and a second vertebra of a patient may comprise implanting a first bone anchor into the first vertebra, the first bone anchor having a proximal portion for engaging a spinal rod and a distal bone engaging portion. The method further comprises implanting a second bone anchor into the second vertebra, the second bone anchor having a proximal portion for engaging a spinal rod and a distal bone engaging portion. The method further comprises connecting an anchor connection instrument to the proximal portion of the first bone anchor and positioning the distal end of a cement delivery tube into a passage provided through at least a portion of the bone engaging portion of the first bone anchor, the anchor connection instrument connecting the cement delivery tube to the first bone anchor. The method further comprises delivering bone cement from a bone cement delivery system coupled to the bone cement delivery tube through the passage in the first bone anchor to the first vertebra, removing the anchor connection instrument and the cement delivery tube from the first bone anchor, connecting the anchor connection instrument and the cement delivery tube to the second bone anchor, delivering bone cement from the bone cement delivery system coupled to the bone cement delivery tube through a passage in bone engaging portion of the second bone anchor to the second vertebra, and connecting a spinal connection element to the first bone anchor and the second bone anchor.

BRIEF DESCRIPTION OF THE FIGURES

These and other features and advantages of the systems and methods disclosed herein will be more fully understood by reference to the following detailed description in conjunction with the attached drawings in which like reference numerals refer to like elements through the different views. The drawings illustrate principles of the systems and methods disclosed herein and, although not to scale, show relative dimensions.

DETAIL DESCRIPTION OF EXEMPLARY EMBODIMENTS

Figure 1:
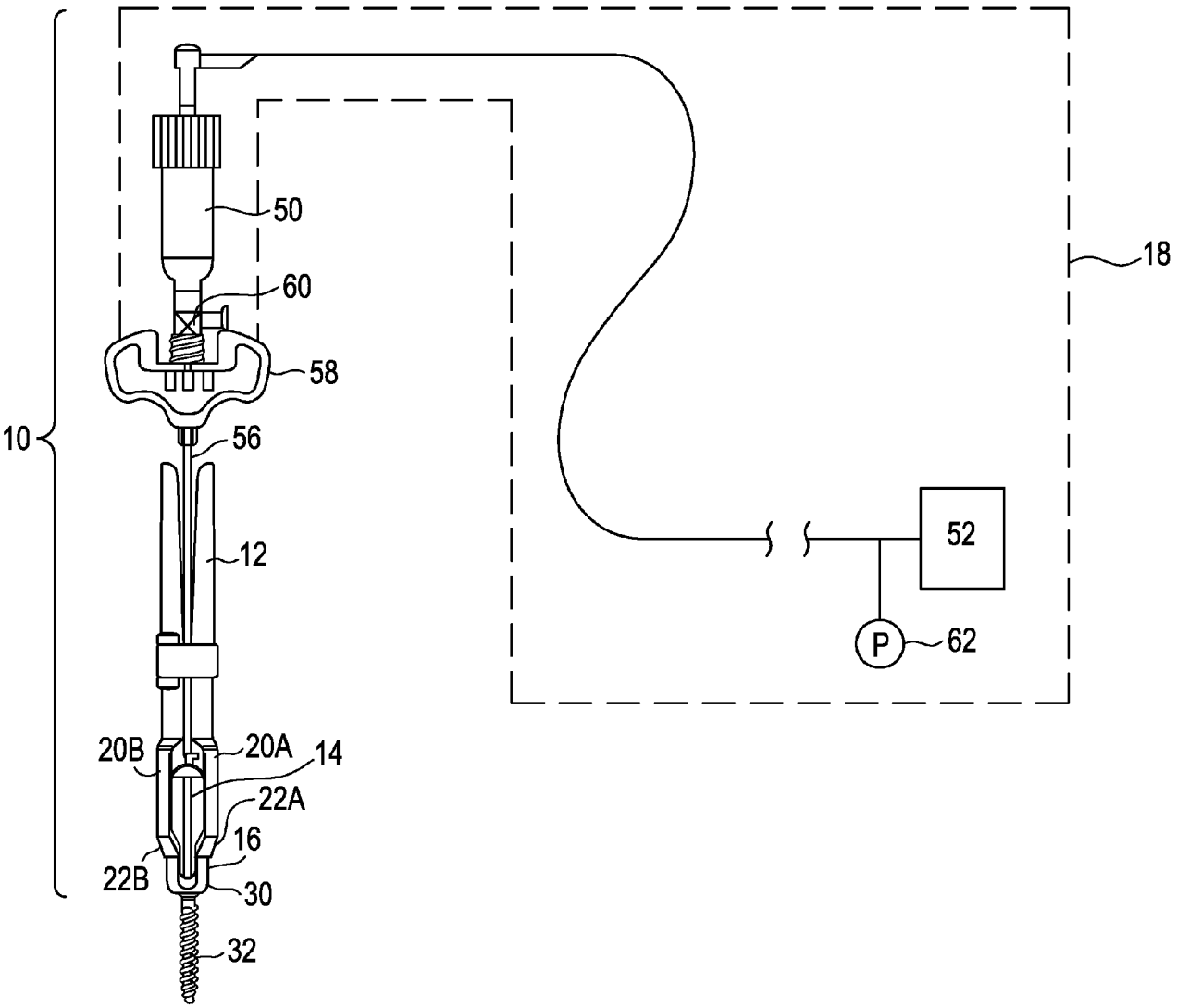
FIG. 1 is a perspective view of an exemplary system for delivering bone cement to a bone anchor, illustrating the system connected to a bone anchor.

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-6 illustrate an exemplary embodiment of a system for delivering bone cement or other materials to a bone anchor. The exemplary system 10 includes an anchor connection instrument 12, a delivery tube 14 connected to the bone anchor 16 by the anchor instrument 12, and a cement delivery system 18 coupled to the cement delivery tube for supplying bone cement to the bone anchor 16. The exemplary system 10 facilitates rapid attachment and removal of the system 10 from a bone anchor such that multiple bone anchors may be provided with bone cement prior to the bone cement setting. The system 10 may be used with any type of bone anchors, including, for example, bone screws used in spine surgery to fix or connect the vertebra of the spine. Such spinal bone screws may include, for example, polyaxial bone screws, monoaxial bone screws, and uniplanar bone screws.

Continuing to refer to FIGS. 1-6, the anchor connection instrument 12 of the exemplary system 10 connects the delivery tube 14 to a bone anchor 16. The exemplary bone anchor 16 is a polyaxial spinal anchor designed for posterior implantation in the pedicle or lateral mass of a vertebra. The exemplary bone anchor 16 includes a proximal portion 30 configured to receive a spinal connection element such as a rigid or dynamic spinal rod and a distal portion 32 configured to engage bone. For example, the proximal portion 30 of the exemplary bone anchor includes a U-shaped rod-receiving slot 31 for receiving a spinal rod. The proximal portion 30 may be configured to receive a closure mechanism, such as, for example, an external nut or cap or an internal setscrew that engages an internal thread 33 provided on the interior of the proximal portion 30 of the bone anchor 16. The proximal portion 30 of the bone anchor 16 may also include features for engaging instruments such as the anchor connection instrument 12. Such features may include one or more openings, such as a slot or the like, for receiving a complementary projection provided on an instrument. In the exemplary bone anchor 16, the proximal portion 30 includes two spaced apart, diametrically opposed slots 35.

The distal bone engaging portion 32 of the exemplary bone anchor 16 includes one or more screw threads. The exemplary bone anchor 16 is polyaxial, e.g., the proximal end portion 30 is connected to the distal bone engaging portion 32 in a polyaxial relationship such that the distal bone engaging portion 32 may be positioned in a plurality of orientations relative to the proximal end portion 30. Exemplary polyaxial spinal anchors include EXPEDIUM polyaxial pedicle screws, VIPER polyaxial pedicle screws, MOSS MIAMI and MOSS MIAMI SI polyaxial pedicle screws, and MOUNTAINEER polyaxial pedicle screws, all of which are available from DePuy Spine, Inc., of Raynham, Mass. Alternative exemplary spine screws include DePuy Spine's EXPEDIUM monoaxial pedicle screws and uniplanar pedicle screws. In addition, exemplary polyaxial pedicle screws are described in U.S. Patent Application Publication Nos. US 2005/0131408 and US 2005/0228388, each of which is incorporated herein by reference.

The exemplary bone anchor 16 is configured to permit bone cement or other materials to be injected into bone through the bone engaging portion 32. A passage 34 extends from the rod receiving slot 31 in the proximal portion 30 of the bone anchor 16 into the distal bone engaging portion 32. The distal bone engaging portion 32 includes one or more openings 36 in the sidewall of the distal bone engaging portion 32. The openings 36 communicate with the passage 34 and extend radially from the passage 34 through the sidewall of the distal bone engaging portion 32. Bone cement or other materials may be injected into bone through the passage 34 and the openings 36.

The anchor connection instrument may be configured to engage a proximal portion 30 of the bone anchor 16 and may connect to an exterior of the bone anchor or, in other embodiments, may connect to the interior of the bone anchor. Exemplary anchor connection instruments are described in US Patent Application Publication Nos. US20050149036, US20050149053, US20060079909, and US20070260261, each of which are incorporated herein by reference. In the illustrated embodiment, the anchor connection instrument 12 connects to the exterior of the proximal portion 30 of the bone anchor 16. The exemplary anchor connection instrument 16 includes a first member 20A and second member 20B that cooperate to selectively connect the instrument to the bone anchor 16. The first member 20A and the second member 20B have distal ends 22A, 22B configured to releasably connect the instrument 12 to the exterior of the proximal portion 30 of the bone anchor 16. For example, the distal ends 22A and 22B may include a projection 24A, 24B for engaging a feature, such as slots 35, in the proximal portion 30 of the bone anchor 16. Alternatively, the distal ends 22A, 22B may include openings to receive a mating feature, such as a projection, provided on the proximal portion of the bone anchor 16. Moreover, in alternative embodiments, the distal end of only one of the members may be configured to engage the bone anchor.

In the exemplary embodiment, the first member 20A is coupled to the opposed second member 20B. The first member 20A and the second member 20B are pivotally connected and pivot about a pivot axis between a release position, in which the first member 20A and the second pivot member 20B pivot away from one another to facilitate removal of the distal ends 22A, 22B of the first member 20A and the second member 20B from the bone anchor and a connect position in which the first member 20A and the second member 20B pivot towards one another and the distal ends 22A, 22B can engage the proximal portion 30 of the bone anchor 16. FIGS. 1-6 illustrate the anchor connection instrument 12 in the connect position. The first member 20A includes a proximal handle 26A and the second member 20B includes a proximal handle 26B. Manipulation of the proximal handles 26A, 26B can effect pivoting of the first member 20A and the second member 20B between the release position and the connect position. For example, movement of the proximal handles 26A and 26B towards one another, in the direction of arrows X in FIG. 3, causes the distal ends 22A, 22B away from one another, in the direction of arrows Y in FIG. 3, to move toward the release position. The first member 20A and the second member 20B may be biased to the release position or to the connect position by a spring or other biasing mechanism.

The anchor connection instrument 12 may be constructed of any biocompatible material suitable for use in medical instruments or implants. For example, the anchor construction instrument 12 may be constructed from a metal, such as stainless steel, or a polymer, such as Radel®. The anchor construction instrument 12 may be a single use device or may be configured for multiple uses after sterilization.

Figure 5:
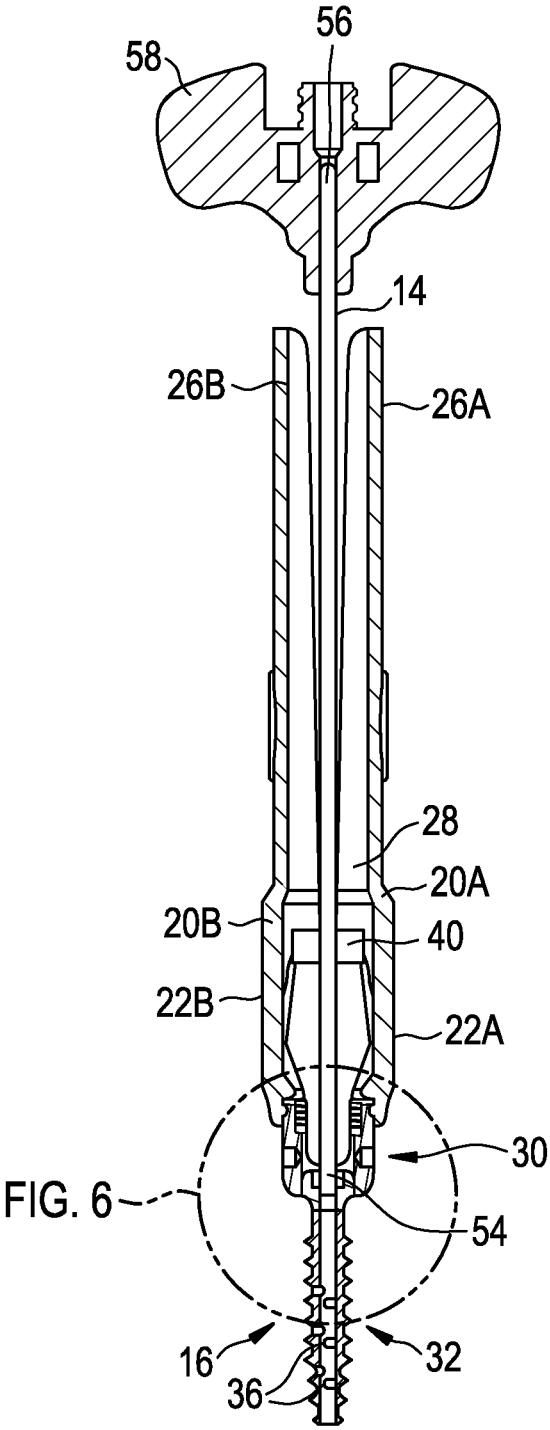
FIG. 5 is a side view in cross section of the system of FIG. 1, illustrating the anchor connection instrument connected to the bone anchor.
Figure 6:
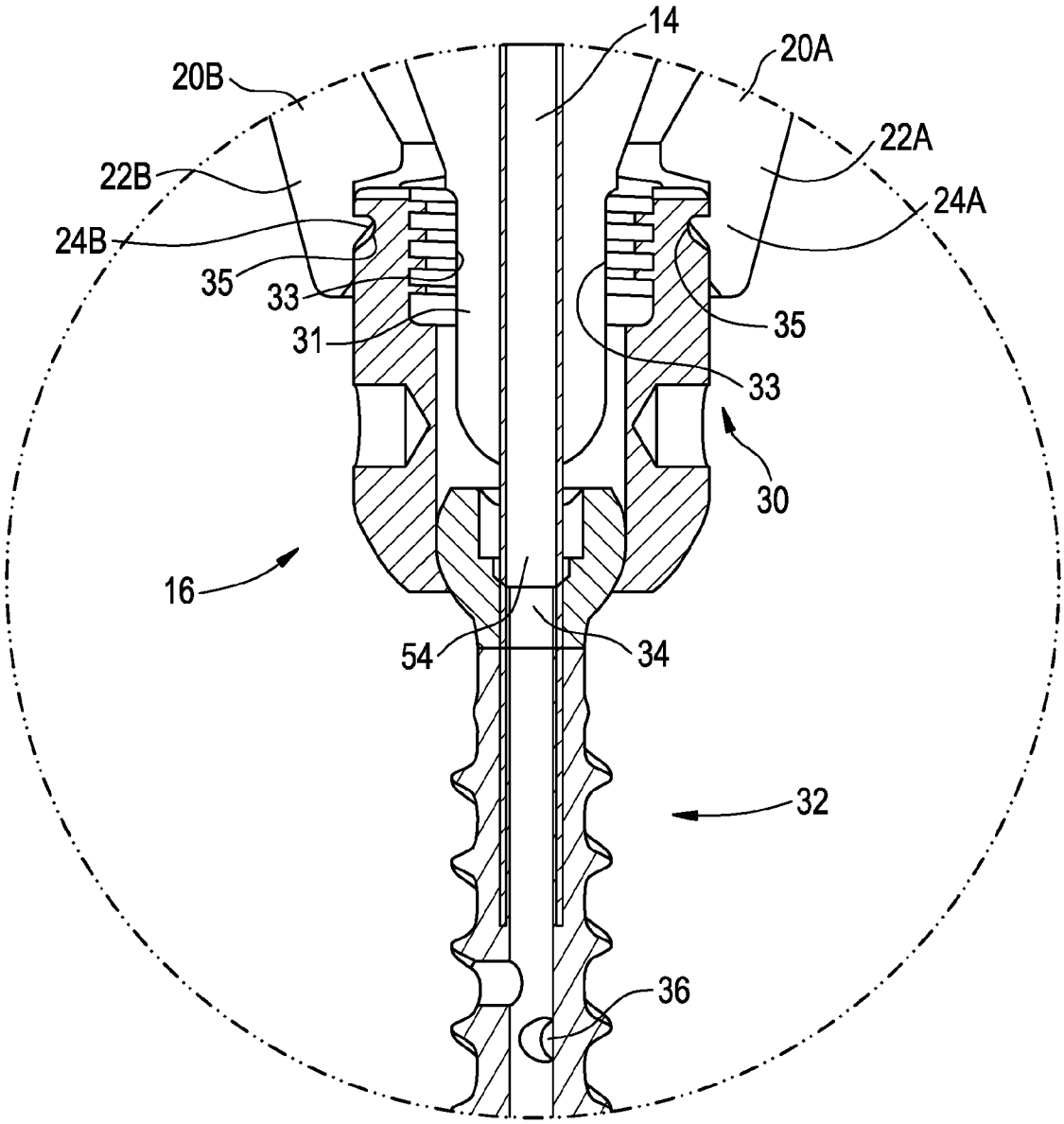
FIG. 6 is a side view in cross section of the system of FIG. 1, illustrating the anchor connection instrument connected to the bone anchor and the cement delivery tube positioned with the passage of the bone anchor.

At least a portion of the first member 20A may be spaced apart from the second member 20B to form a passage 28 therebetween for receiving the cement delivery tube 14. A tube connector 40 may be positioned within the passage 28 between the first member 20A and the second member 20B, as illustrated in FIG. 5. The tube connector 40 may have an opening sized to receive the cement delivery tube 14 therethrough. The opening in the tube connector 40 is preferably sized to permit the cement delivery tube 14 to move along a longitudinal axis of the tube 14 relative to the anchor connection instrument 12 while concomitantly restricting motion of the tube 14 in a direction transverse to the longitudinal axis of the tube 14. For example, the opening in the tube connector 14 has an extent, e.g., a diameter, approximate to the extent, e.g. the outer diameter, of the cement delivery tube 14. In the exemplary embodiment, the tube connector 40 is generally disk shaped, is constructed of an elastomeric polymer material, and has a central opening having a diameter less than or equal to the outer diameter of the cement delivery tube 14.

The cement delivery tube 14 is removably coupled to a cement delivery system 18. The cement delivery system 18 may include a reservoir 50 or other container for holding and/or mixing the cement and a pressure source 52, such as a pump, for applying pressure to the bone cement in the reservoir 50 to move the bone cement through the system 18, and the tube 14, relative to the reservoir 50. A suitable cement delivery system 50 is the CONFIDENCE spinal cement system, available from DePuy Spine, Inc. of Raynham, Mass., and the cement delivery systems described in the following U.S. patents and patent applications: U.S. Pat. No. 7,097,648 and U.S. Patent Application Publication Nos. U.S. 2008/0228192, U.S. 2006/0264967, U.S. 2006/0079905, U.S. 2007/0027230, U.S. 2008/0212405, U.S. 2007/0032567, and U.S. 2008/0200915 and U.S. patent application Ser. Nos. 09/890,172 and 11/561,969, each of which is incorporated herein by reference.

The bone cement delivery tube 14 is coupled to the bone cement delivery system 18 to permit bone cement to be introduced to the delivery tube 14 from the system 18. In the exemplary embodiment, the bone cement delivery tube 14 is an elongated hollow tube having a distal end 54 sized for insertion into the passage 34 in the distal portion 32 of the bone anchor 16 and a proximal end 56 having a handle 58 to facilitate manipulation of the tube 14. The proximal end 56 of the tube may extend through the handle 58 and terminate at connection feature, such as a luer lock connection, that permits connection to the bone cement delivery system 18. The cement delivery tube 14 may be a needle or stylet having a diameter less than the diameter of the passage 34 in the distal portion 32 of the bone anchor 16. The cement delivery tube 14 may be constructed from any biocompatible material suitable for use in medical instruments or implants. For example, the cement delivery tube 14 may be constructed from a metal, such as stainless steel, or a polymer, such as Radel®. The cement delivery tube 14 may be a single use device or may be configured for multiple uses after sterilization. In one exemplary embodiment, the anchor connection instrument 12, including the tube connector 40, and the cement delivery tube 14, may be prepackaged in an assembled, sterilized state with the cement delivery tube 14 positioned with the anchor connection instrument 12 and through the tube connector 40.

In the exemplary embodiment, the reservoir 50 of the cement delivery system 18 is directly connected to the cement delivery tube 14 and the pressure source 52 may be positioned remote from the cement reservoir 50 and the cement delivery tube 14. Remote placement of the pressure source 52 permits a medical professional to inject cement into the bone anchor 16 outside of the imaging field of the imaging system (e.g., a fluoroscopy or x-ray system) used to monitor the cement volume injected into the patient's bone thorough the bone anchor. In this manner, the medical professional is not exposed to radiation from the imaging system during the bone cement injection procedure.

The cement delivery system 18 may include a valve 60 for controlling cement delivery to the cement delivery tube 14. For example, the valve 60 may be used to selectively interrupt flow of bone cement to the bone cement delivery tube 14. In the exemplary embodiment, the valve 60 is positioned at the interface between the cement delivery system 18 and the tube 14, e.g., between the cement reservoir 50 and the proximal end 56 of the cement delivery tube 14. In alternative embodiments, a valve may be provided as part of the cement delivery tube 14, for example, in the handle 58 or at the distal end 54 of the tube 14. For example, in one exemplary embodiment, at least a portion of the distal end 54 or other portion of the tube, may be compressible and the valve may be operated to selectively compress the compressible portion and thereby restrict cement flow through the tube. Such an embodiment is described in more detail below.

An exemplary method of stabilizing a first vertebra and second vertebra of a patient, including delivering of bone cement to a bone anchor, will be described in more detail below. Initially, a first bone anchor, such as bone anchor 16 described above, may be implanted into a first vertebra and a second bone anchor, such as another bone anchor 16, may be implanted in a second vertebra. For example, the first and second bone anchors may be implanted into the respective pedicles of adjacent vertebrae through a posterior approach. The implantation procedure may be an open procedure, in which, for example, the bone anchors are implanted through a single incision, or a minimally invasive procedure in which the first bone anchor and the second bone anchor are implanted through separate percutaneous incisions.

The anchor connection instrument 12 may be connected to the proximal portion 30 of the first bone anchor. For example, the distal end 22A of the first member 20A of the anchor connection instrument 12 may be moved, e.g., pivoted, away from the distal end 22B of the second member 20B of the anchor connection instrument 12 to separate the distal end 22A of the first member 20A from the distal end 22B of the second member 20B. The separated distal ends 20A and 20B may then be positioned about the proximal end 30 of the bone anchor. The distal end 22A of the first member 20A of the anchor connection instrument 12 may be moved, e.g., pivoted, toward the distal end 22B of the second member 20B of the anchor connection instrument 12 until the distal ends 22A and 22B contact the proximal end 30 of the first bone anchor to connect the anchor connection instrument 12 to the first bone anchor.

Figure 2:
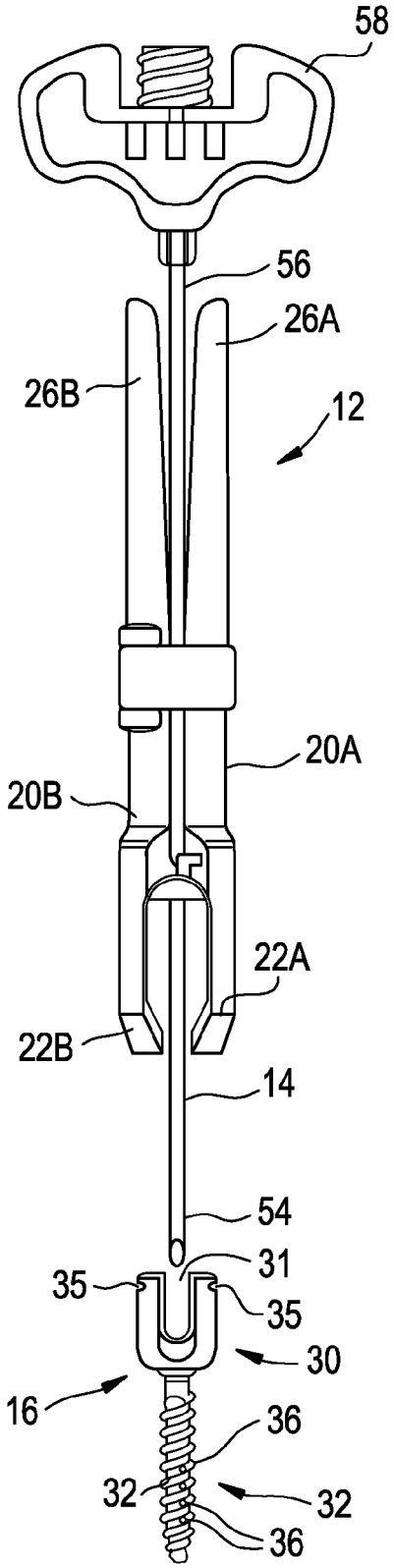
FIG. 2 is a perspective view of the system of FIG. 1, illustrating the anchor connection instrument and the cement delivery tube prior to connection to the bone anchor.
Figure 3:
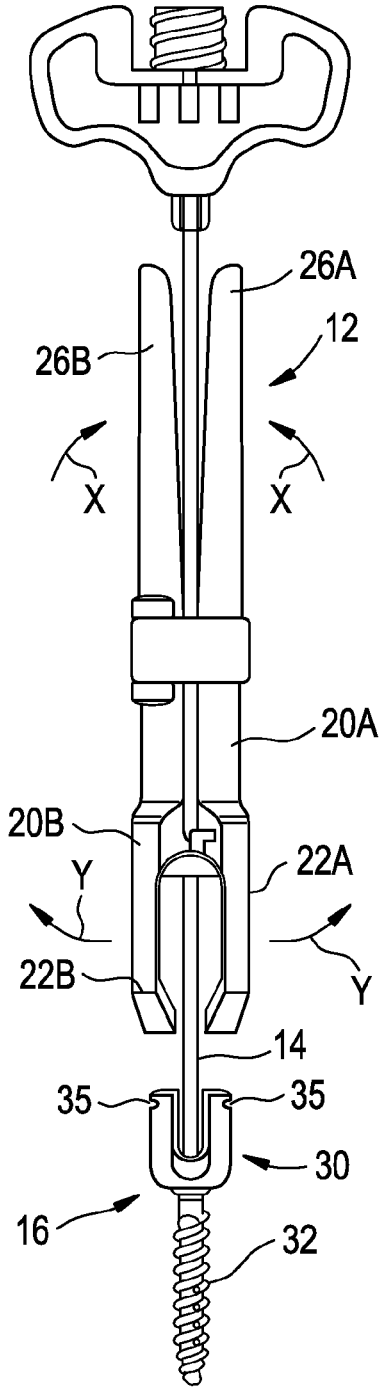
FIG. 3 is a perspective view of the system of FIG. 1, illustrating the bone cement delivery tube inserted into the passage of the bone anchor.
Figure 4:
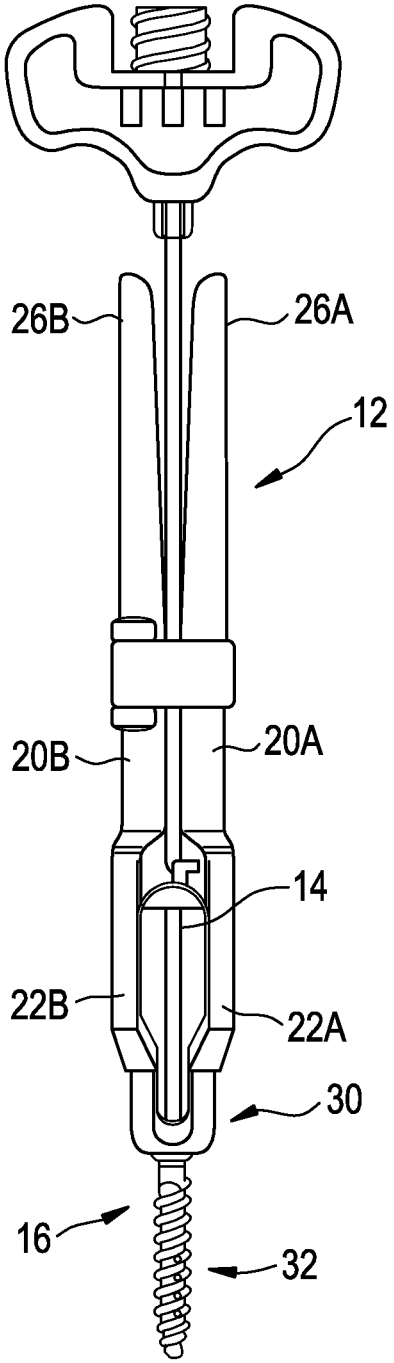
FIG. 4 is a perspective view of the system of FIG. 1, illustrating the distal end of the anchor connection instrument connected to the bone anchor.

As illustrated in FIG. 2, the cement delivery tube 14 may be coupled to the anchor connection instrument 12 via the tube connector 40 prior to attachment of the anchor connection instrument 12 to the first bone anchor 12. The distal end 54 of the cement delivery tube 14 may be positioned in the passage 34 of the distal bone engaging portion 32 of the first bone anchor 12. In one exemplary embodiment, the distal end 54 of the cement delivery tube 14 may be adjusted relative to one or more openings 36 in the distal portion 34 of the first bone anchor to select the opening or openings through which to deliver cement to the first vertebra.

The cement delivery tube 14 may be coupled to the cement delivery system 18 before or after connection of the cement delivery tube 14 and the anchor connection instrument 12 to the bone anchor. In one embodiment, the bone cement may be mixed in the reservoir 50 of the cement delivery system 18 prior to connection to the cement delivery tube 14. In cement delivery systems 18 including a valve 60, the valve may be opened to permit cement flow through the cement delivery tube 14. The pressure source 52 may be operated to deliver a fluid, such as saline, under pressure to the reservoir 50 which forces bone cement from the reservoir 50 into the bone cement delivery tube 14, through the passage 54 in the first bone anchor to the first vertebra.

The medical professional operating the pressure source 52 may monitor the delivery of cement to the first vertebra using an imaging system such as a fluoroscopy system. Because the pressure source 52 is remote from the anchor connection instrument 14 and is outside the imaging field, the medical professional is not exposed to radiation from the imaging system.

Once the desired amount of bone cement is delivered to the first vertebra, the anchor connection instrument 12 and cement delivery tube 14 may be removed from the first bone anchor and connected to the second bone anchor, preferably while the cement delivery tube 14 remains connected to the cement delivery system 18. Prior to disconnecting the anchor connection instrument 12 and the cement delivery tube 14 from the first bone anchor, the valve 60, if provided, may be closed to interrupt cement delivery to the first bone anchor and the cement delivery tube 14. In addition, the pressure source 52 may be operated in reverse, for example to provide for fluid flow in the direction of the pressure source, to reduce pressure of the bone cement in cement delivery tube 14 and to minimize leaking of cement from the distal end 54 of the cement delivery tube 14 during removal. The fluid pressure in the cement delivery system 18 may be monitored through a pressure indicator 62.

Once the anchor connection instrument 12 and cement delivery tube 14 are connected to the second bone anchor, bone cement may be delivered to the second bone anchor and the second vertebra in accordance with the procedure described above in connection with the first bone anchor and the first vertebra. Once the desired amount of cement is delivered to the second vertebra, the anchor connection instrument 12 and the cement delivery tube 14 may be removed from the second bone anchor. A spinal connection element, such as a spinal rod may then be connected to the first bone anchor and the second bone anchor to stabilize the first vertebra relative to the second vertebra. In a minimally invasive procedure, the spinal connection element may be delivered to first bone anchor through the percutaneous incision in which first bone anchor is implanted and the spinal connection element may be positioned beneath the skin and the lamina to the second bone anchor. Such a minimally invasive procedure may be carried out using the VIPER and VIPER II Spinal Fixation Systems available from DePuy Spine of Raynham, Mass.

Bone cement may be injected through any number of bone anchors, e.g., one or more bone anchors depending on, for example, the procedure being performed and the quality of the bone of the vertebra being stabilized. The exemplary systems and methods described above allow multiple anchors and their respective vertebrae to be quickly and easily filled with bone cement. Moreover, since bone cement typically has a limited working time in which the cement is flowable and suitable for injection, the system and methods described above allow an increased number of anchors to be injected with cement during the bone cement working time.

The exemplary systems and methods described above are particularly suited for delivering bone cement. Although any type of bone cement or bone filler may be used with these systems and methods, a high viscosity bone cement, such as high viscosity polymethylmethacrylate based cement available from DePuy Spine, Inc., of Raynham Mass. (CONFIDENCE Spinal Cement), is particularly suited for delivery using the above systems and methods. Alternatively, the systems and methods described above may be used to deliver other materials, such as irrigation fluid or biologics to bone through a bone anchor.

Figure 7A:
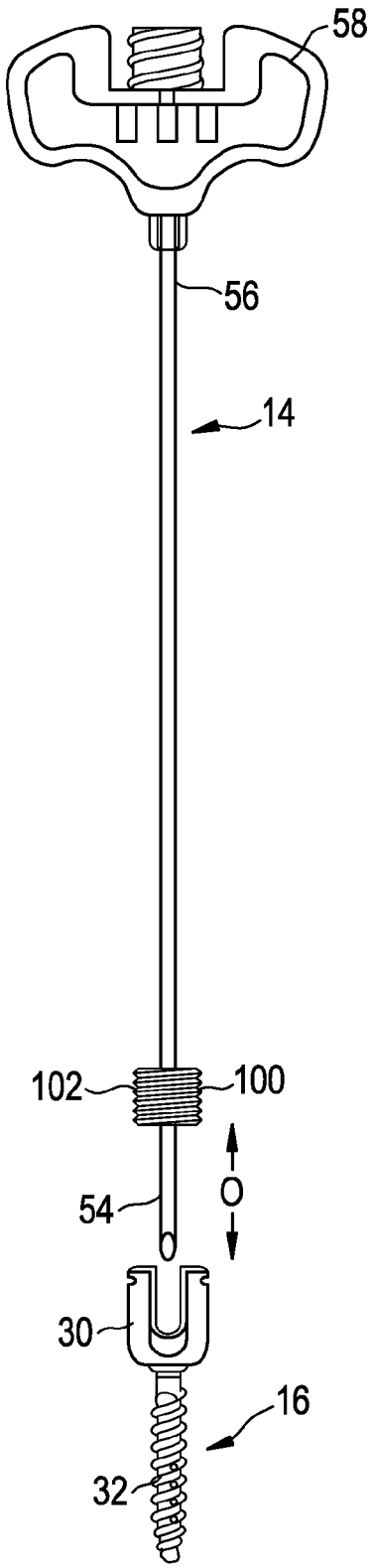
FIGS. 7A-7D are perspective views of another exemplary system for delivering bone cement to a bone anchor, illustrating the connection of the system to a bone anchor.
Figure 7B:
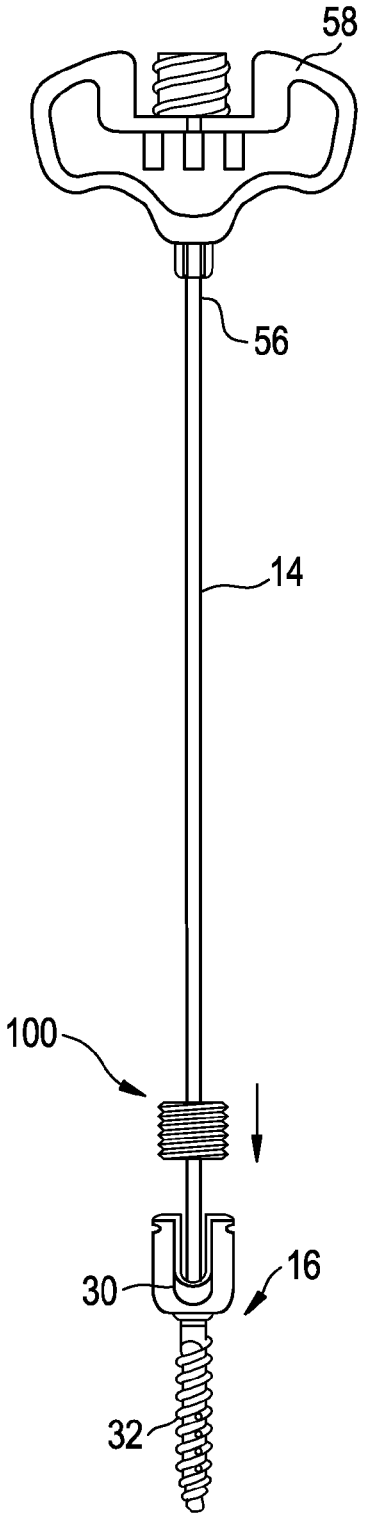
Figure 7C:
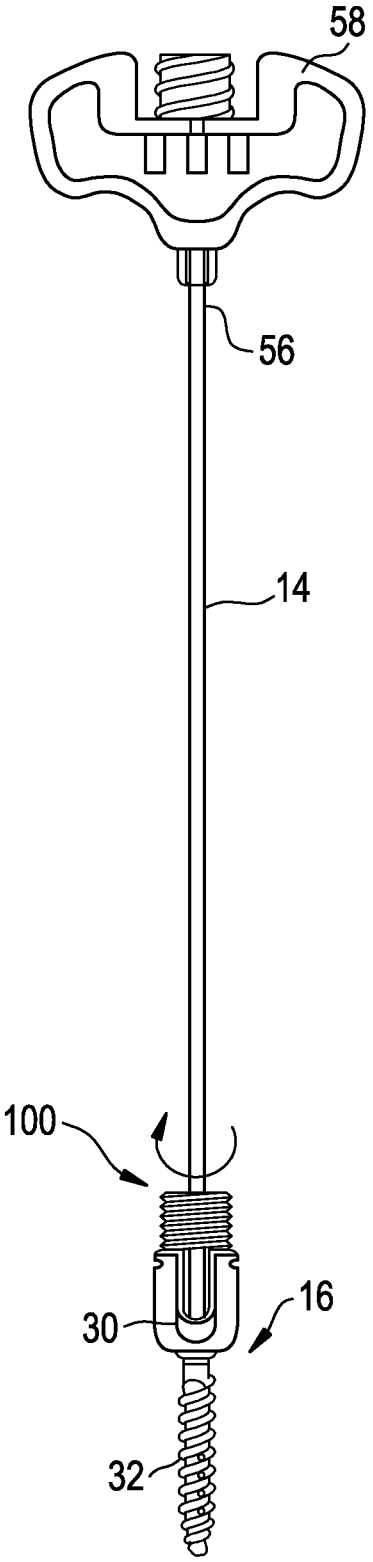
Figure 7D:
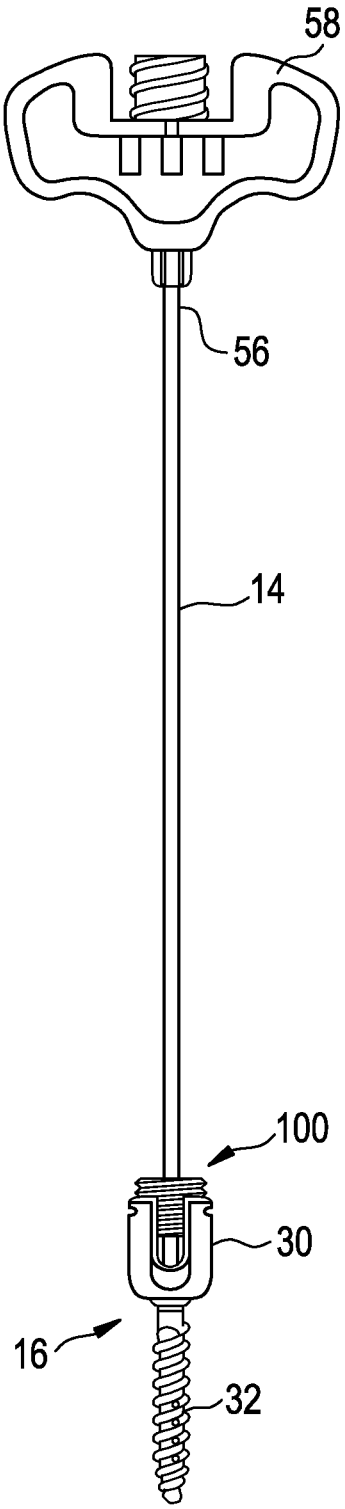

FIGS. 7A-7D illustrate another exemplary embodiment of a system for delivering bone cement or other materials to a bone anchor. In the exemplary system, the cement delivery tube 14 includes a connection member 100 positioned between the proximal end 56 of the tube 14 and the distal end 54 of the tube 14. The connection member 100 is configured to engage the internal thread 33 provided on the proximal portion 30 of the bone anchor 16. In the exemplary embodiment, the connection member 100 is generally disk shaped and includes an external thread 102 complementary to the internal thread 33 provided on the proximal portion 30 of the bone anchor 16. The connection member 100 may be spaced a distance D from the tip of the distal end 54 of the tube 14 selected to allow the distal end 54 of the tube 14 to advance into the passage 34 provided in the bone anchor 16, as illustrated in FIG. 7A. In use, the cement delivery tube 14 may be connected to the bone anchor 16 by advancing the distal end 54 of the tube 14 into the passage 34 of the bone anchor, as illustrated in FIG. 7B, and rotating the tube 14 to engage the thread 102 on the connection member 100 with the internal thread 33 of the bone anchor 16, as illustrated in FIG. 7C. The tube 14 may be rotated until the distal end 54 of the tube 14 reaches the desired depth within the passage 34 of the bone anchor 16, as illustrated in FIG. 7D. The tube 14 may be quickly removed from the bone anchor 16 by rotating the tube 14 in the opposite direction to disengage thread 102 from thread 33. The tube 14 may be connected to a cement delivery system such as the cement delivery system 18 described above and cement may be injected through one or more bone anchors in a manner analogous to the methods described above.

Figure 8A:
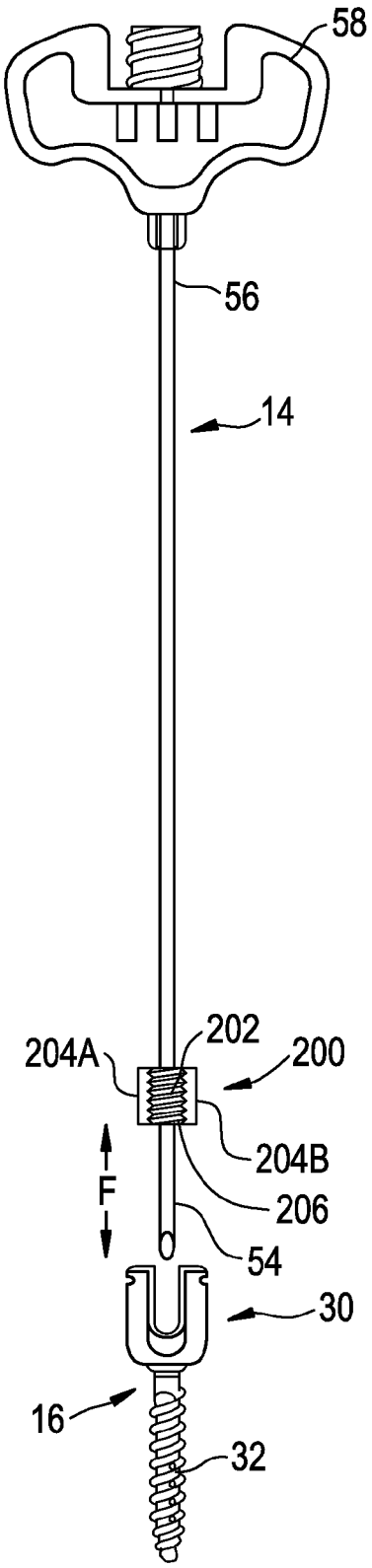
FIGS. 8A-E are perspective views of another exemplary system for delivering bone cement to a bone anchor, illustrating the connection of the system to a bone anchor.

FIGS. 8A-10 illustrate another exemplary embodiment of a system for delivering bone cement or other materials to a bone anchor. In the exemplary system, the cement delivery tube 14 includes a connection member 200 positioned between the proximal end 56 of the tube 14 and the distal end 54 of the tube 14. Like the connection member 100 described above, the connection member 200 is configured to engage the internal thread 33 provided on the proximal portion 30 of the bone anchor 16. In the exemplary embodiment, the connection member 200 is generally disk shaped and includes an external thread 202 complementary to the internal thread 33 provided on the proximal portion 30 of the bone anchor 16. In the exemplary embodiment, the thread 202 of the connection member 200 is interrupted at two spaced apart, opposed unthreaded sections 204A and 204B. The unthreaded sections [202A and 202B] *204A and 204B* are positioned diametrically opposed to one another. Thus, the connection member 200 has a threaded section 206 interposed between each unthreaded section [202A and 202B] *204A and 204B*. The connection member 200 may be spaced a distance F from the tip of the distal end 54 of the tube 14 selected to allow the distal end 54 of the tube 14 to be advanced into the passage 34 provided in the bone anchor 16, as illustrated in FIG. 8A.

Figure 8B:
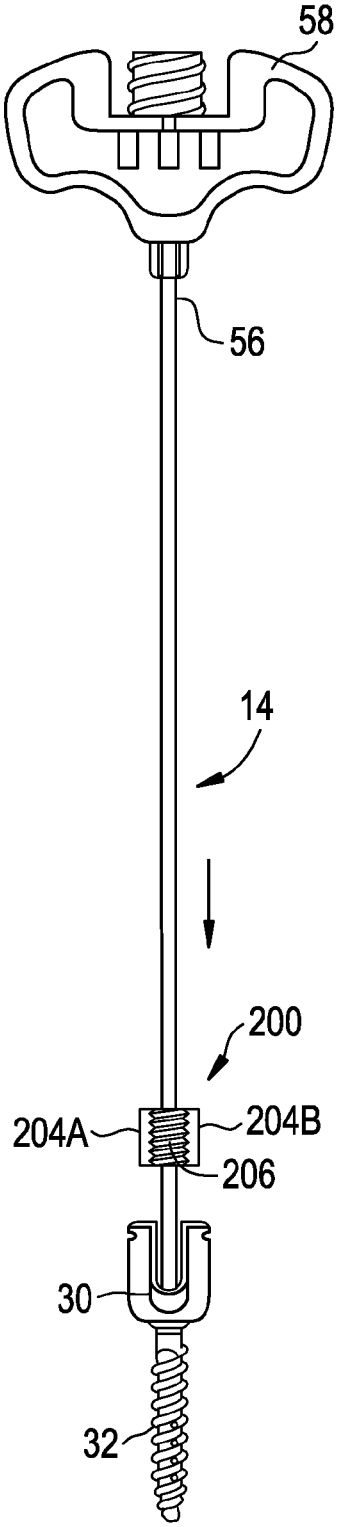
Figure 8C:
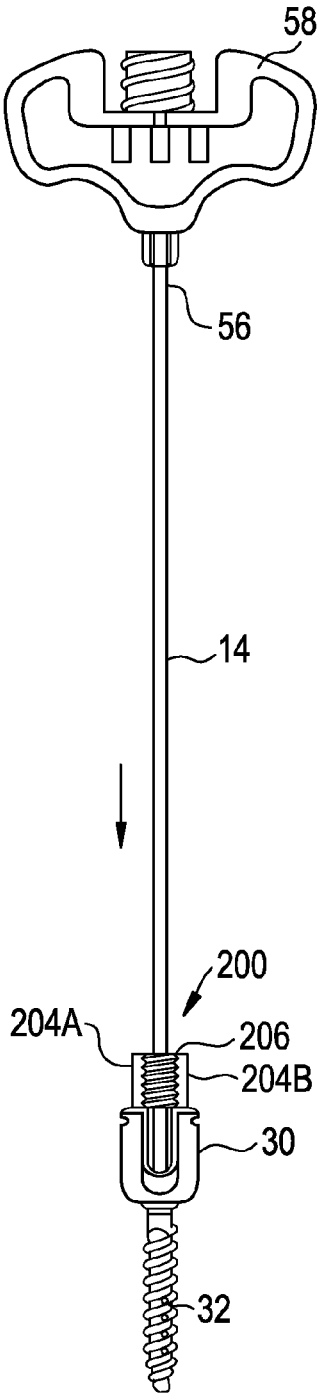
Figure 8D:
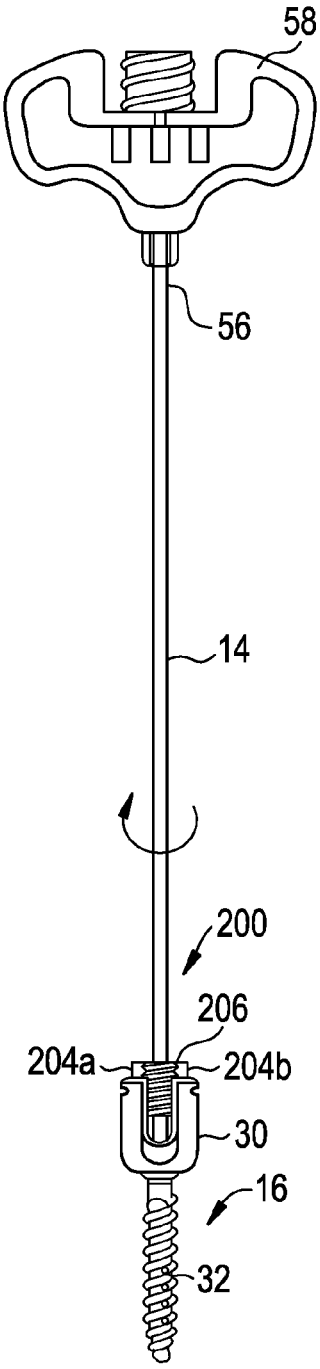
Figure 8E:
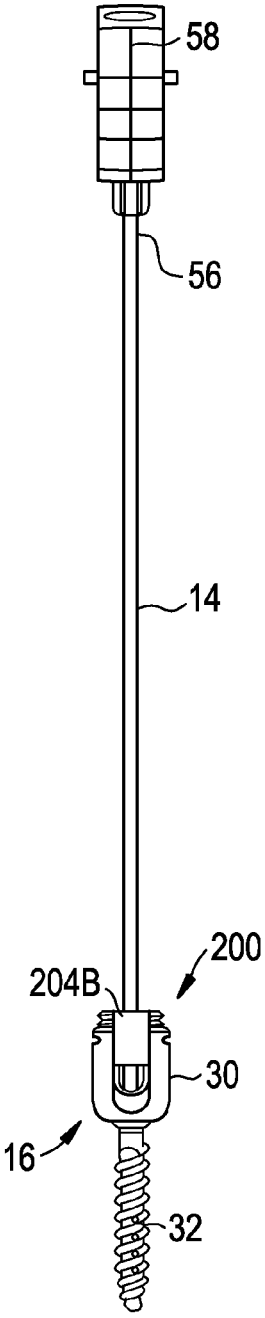
Figure 9:
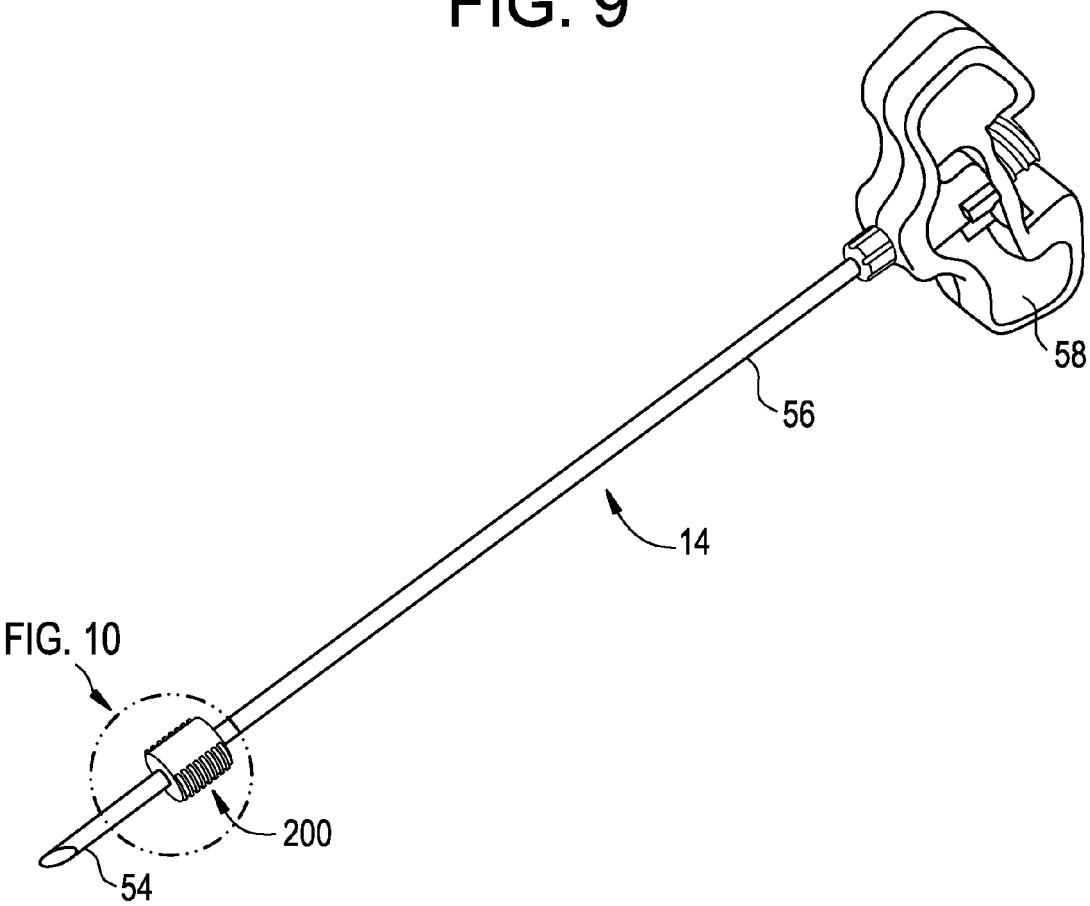
FIG. 9 is a perspective view of the system of FIGS. 8A-8E.
Figure 10:
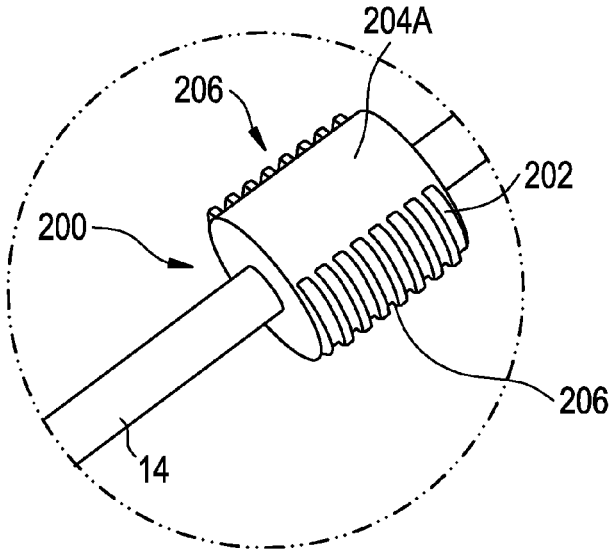
FIG. 10 is a perspective view of the connection member of the system of FIGS. 8A-8E.

In use, the cement delivery tube 14 may be connected to the bone anchor 16 by advancing the distal end 54 of the tube 14 into the passage 34 of the bone anchor 16, as illustrated in FIG. 8B. During insertion of the tube 14, the connection member 200 is oriented such that the unthreaded sections 204A and 204B face the internally threaded portions of the proximal portion 30 of the bone anchor 16 and the threaded sections 206 are aligned with the rod slot 31 of the proximal portion 30 of the one anchor 16, as illustrated in FIGS. 8C-D. Once the distal end 54 of the tube 14 reaches the desired depth within the passage 34 of the bone anchor 16, the tube 14 may be rotated approximately 90° to engage the thread 202 on the threaded portions 206 with the internal thread 33 on the threaded portions of the bone anchor 16, as illustrated in FIG. 8E. The tube 14 may be quickly removed from the bone anchor 16 by rotating the tube 14 approximately 90° in the opposite direction to disengage the thread 202 on the threaded portions 206 from thread 33. The tube 14 may be connected to a cement delivery system such as the cement delivery system 18 described above and cement may be injected through one or more bone anchors in a manner analogous to the methods described above.

Figure 11A:
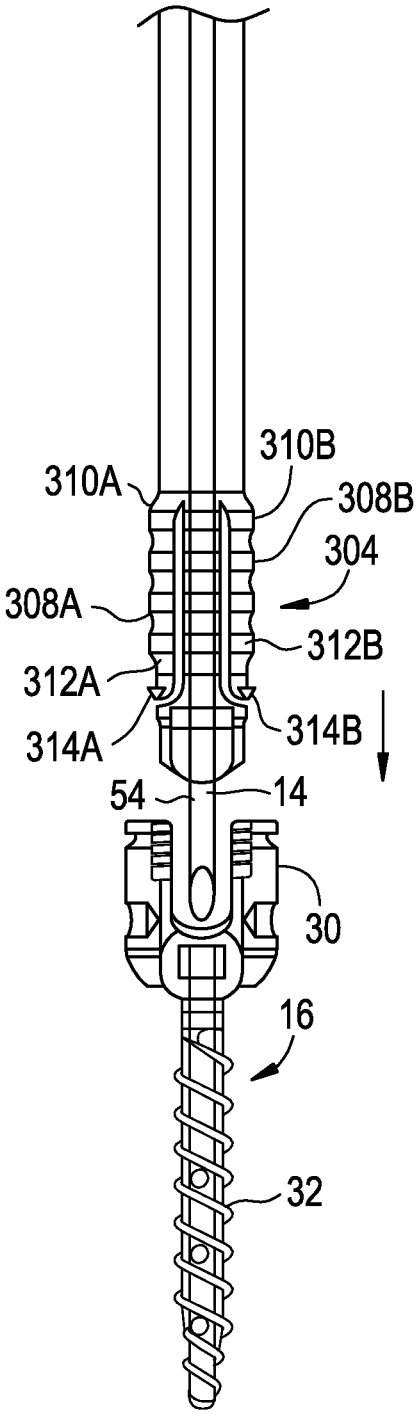
FIGS. 11A-11B are perspective views of another exemplary system for delivering bone cement to a bone anchor, illustrating the connection of the system to a bone anchor.
Figure 11B:
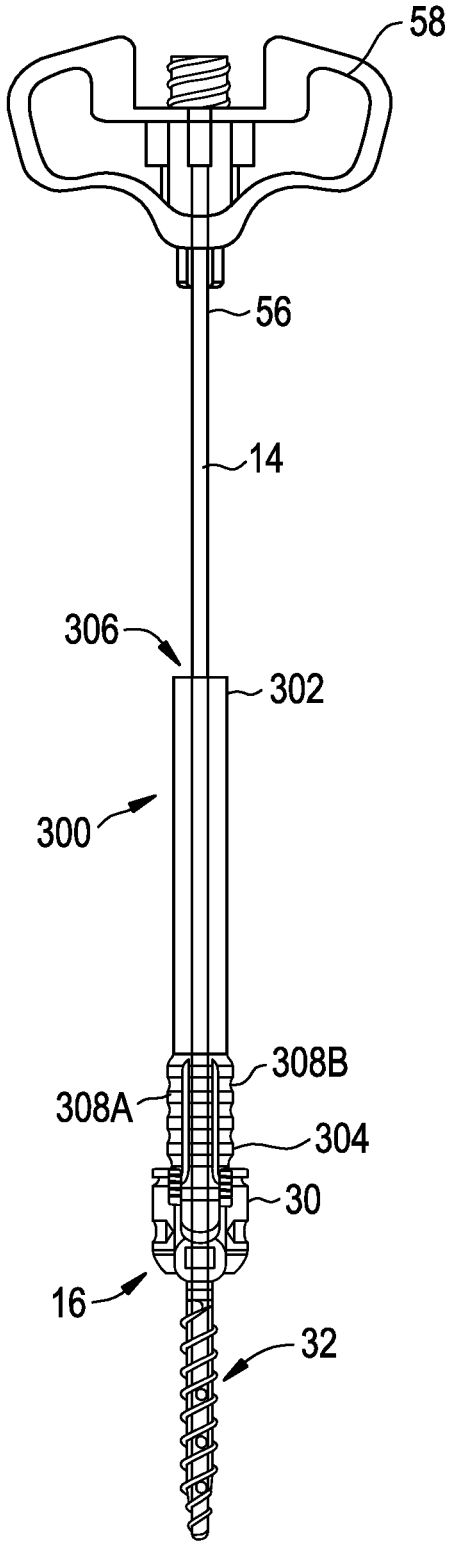

FIGS. 11A-11B illustrate another exemplary embodiment of a system for delivering bone cement or other materials to a bone anchor. In the exemplary system, the cement delivery tube 14 may be connected to bone anchor 16 with an anchor connection instrument 300 configured to engage the interior of the proximal portion 30 of the bone anchor 16. The exemplary anchor connection instrument 300 is generally tubular in shape and has a proximal end 302, a distal end 304, and an internal lumen or passage 306 extending from the proximal end 302 and the distal end 304 for receiving the cement delivery tube 14 therein. The distal end 304 of the anchor connection instrument 300 includes two spaced-apart prongs or fingers 308A and 308B configured to selectively engage the thread 33 on the proximal portion 30 of the bone anchor 16. The prongs 308A and 308B are diametrically opposed to each other and are connected at a proximal end 310A, 310B to the anchor connection instrument 300. The prongs 308A and 308B have a free distal end 312A, 312B opposite the proximal ends 310A, 310B. Each prong 308A, 308B may pivot or flex about its proximal end 310A,B between a first, spaced-apart position, illustrated in FIG. 11A and a second, compressed position in which the prongs 308A, 308B pivot towards one another to facilitate insertion of the distal end 304 of the instrument 300 into the bone anchor. The prongs 308A, 308B are biased to the first position. The distal ends 312A, 312B of each prong 308A, 308B includes a projection 314A, 314B for engaging the internal thread 33 of the bone anchor 16.

In use, the anchor connection instrument 300 and the tube 14 may be advanced toward the bone anchor 16 to position the distal end 54 of the tube 14 within the passage 34 of the bone anchor 16, as illustrated in FIG. 11A. As the distal end 304 of the instrument 300 engages the proximal portion 30 of the bone anchor 16, the prongs 308A and 308B are compressed to the first, compressed position. The projections 314A and 314B may include a ramped surface to compress the prongs 308A, 308B toward the second position. In the second position, the projections 314A, 314B may pass the leading edge of the thread 33 of the bone anchor 16 and then snap into place beneath a crest of the thread 33 as the prongs 308A, 308B move to the first position thereby connecting the anchor connection instrument 300 and the tube 14 to the bone anchor. The anchor connection instrument 300 may be removed from the bone anchor 16 by compressing the prongs 308A, 308B to the second position and retracting the distal end 304 from the proximal portion 30 of the bone anchor 16. The tube 14 may be connected to a cement delivery system such as the cement delivery system 18 described above and cement may be injected through one or more bone anchors in a manner analogous to the methods described above.

Figure 12A:
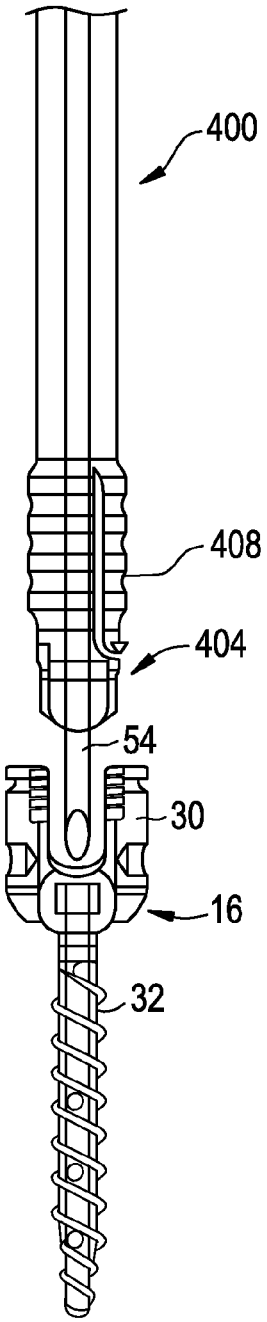
FIGS. 12A-12C are perspective views of another exemplary system for delivering bone cement to a bone anchor, illustrating the connection of the system to a bone anchor.
Figure 12B:
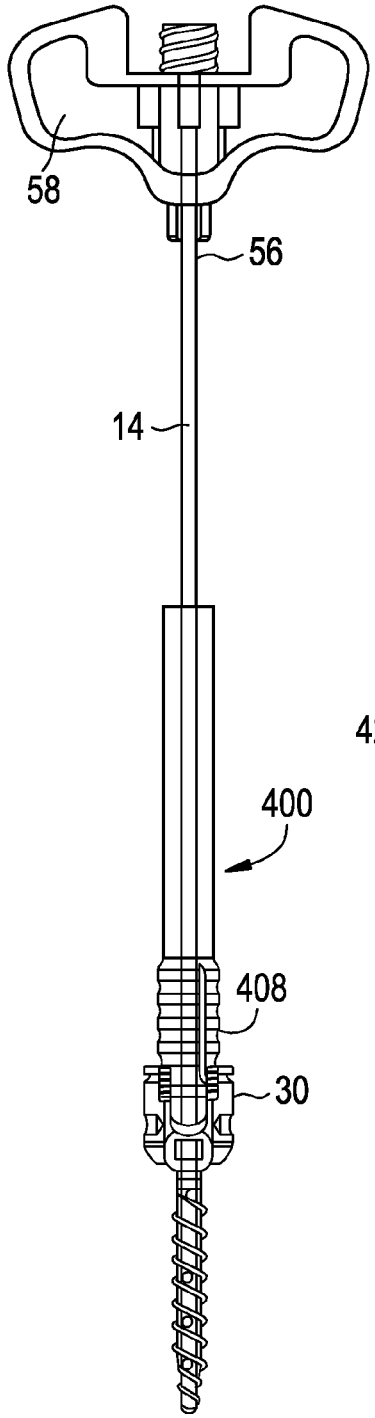
Figure 12C:
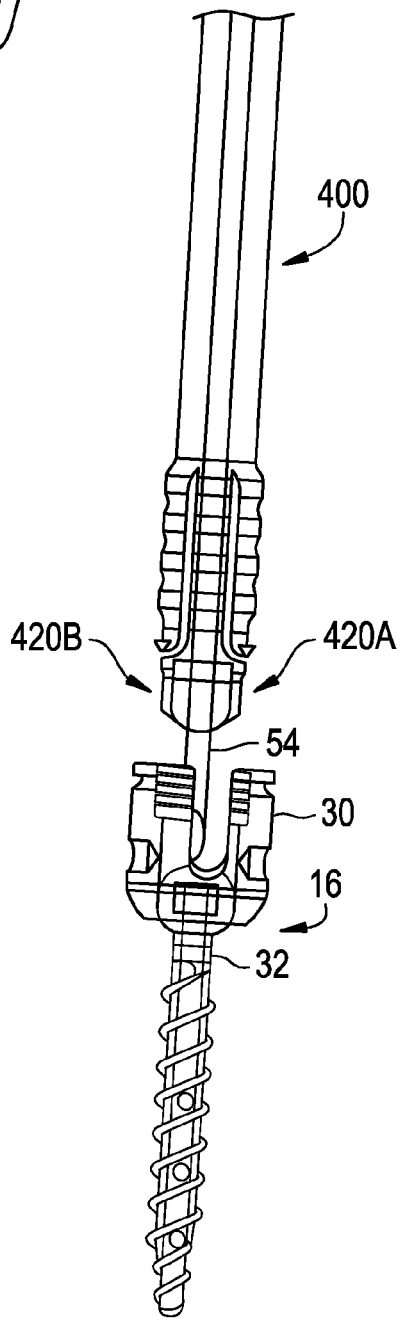
Figure 13A:
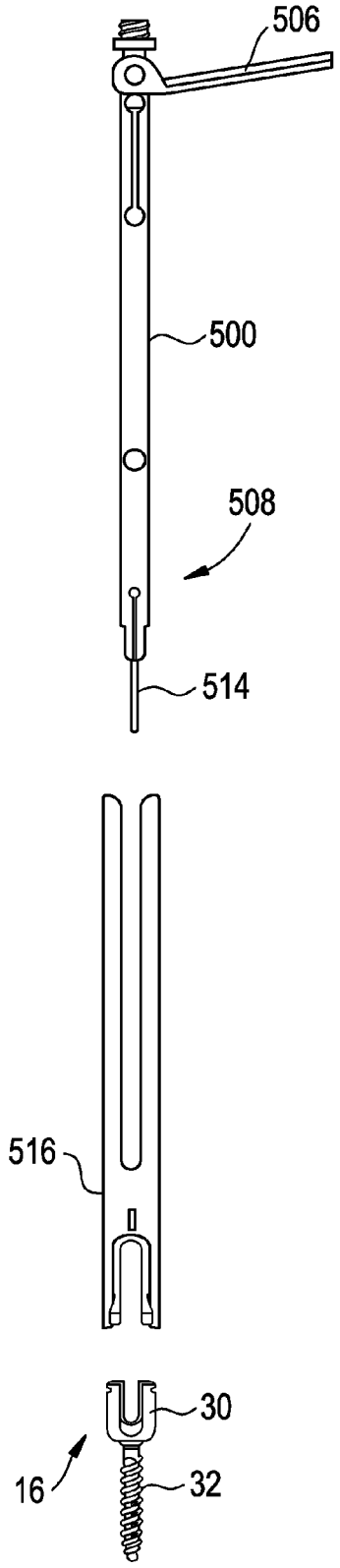
FIGS. 13A-F are perspective views of another exemplary system for delivering bone cement to a bone anchor, illustrating the connection of the system to a bone anchor.
Figure 13B:
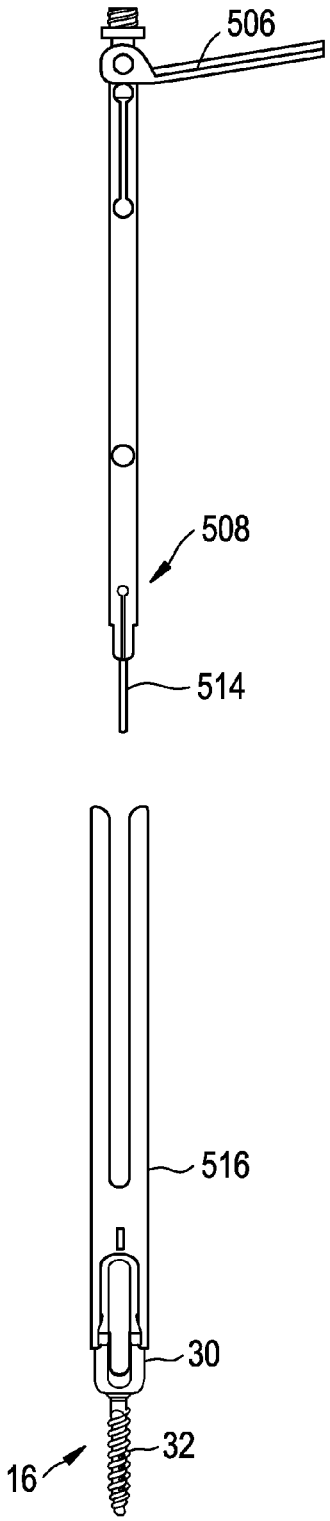
Figure 13C:
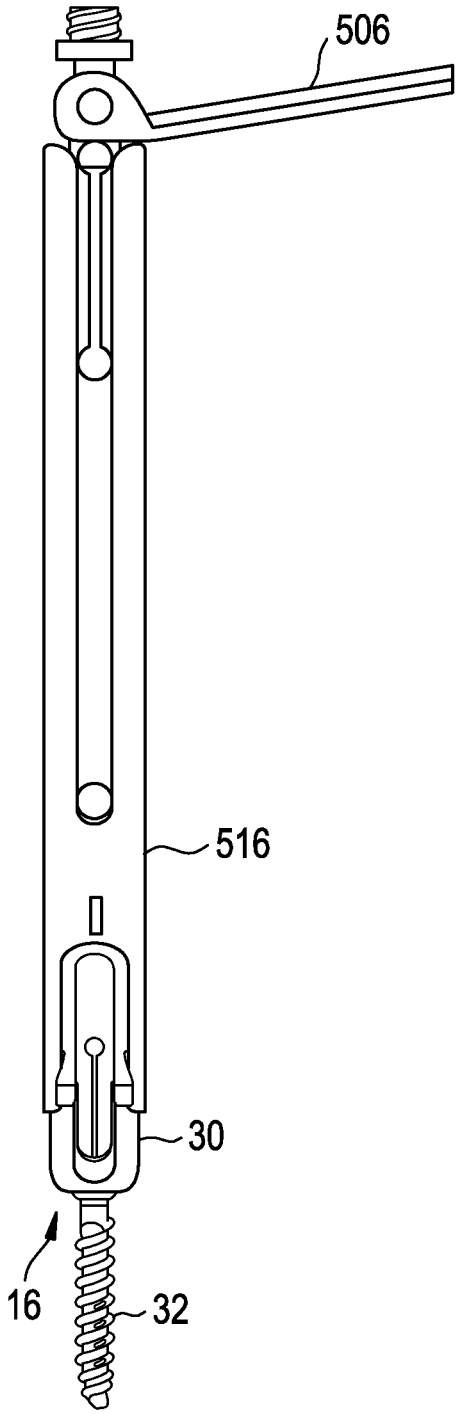
Figure 13D:
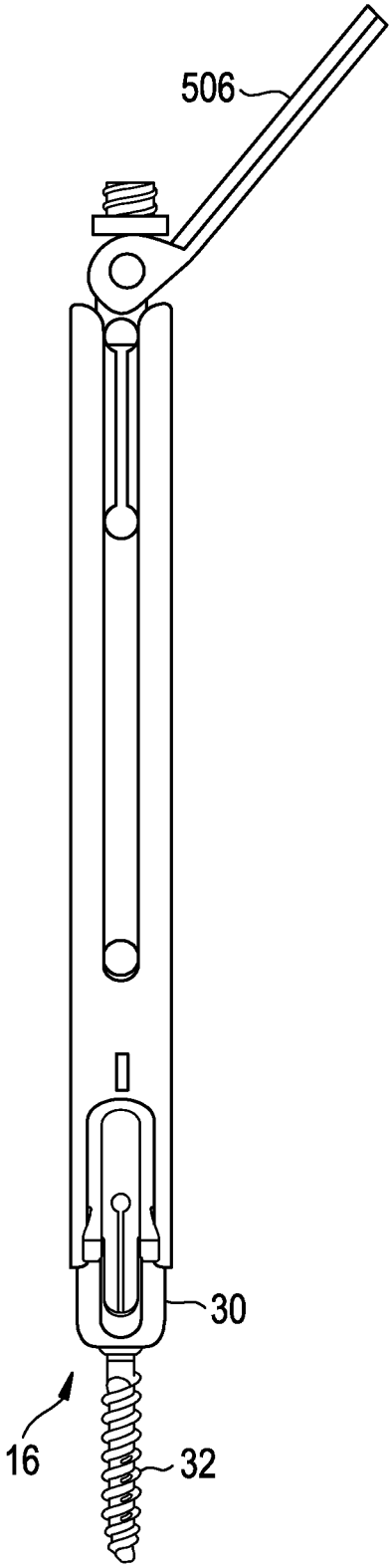
Figure 13E:
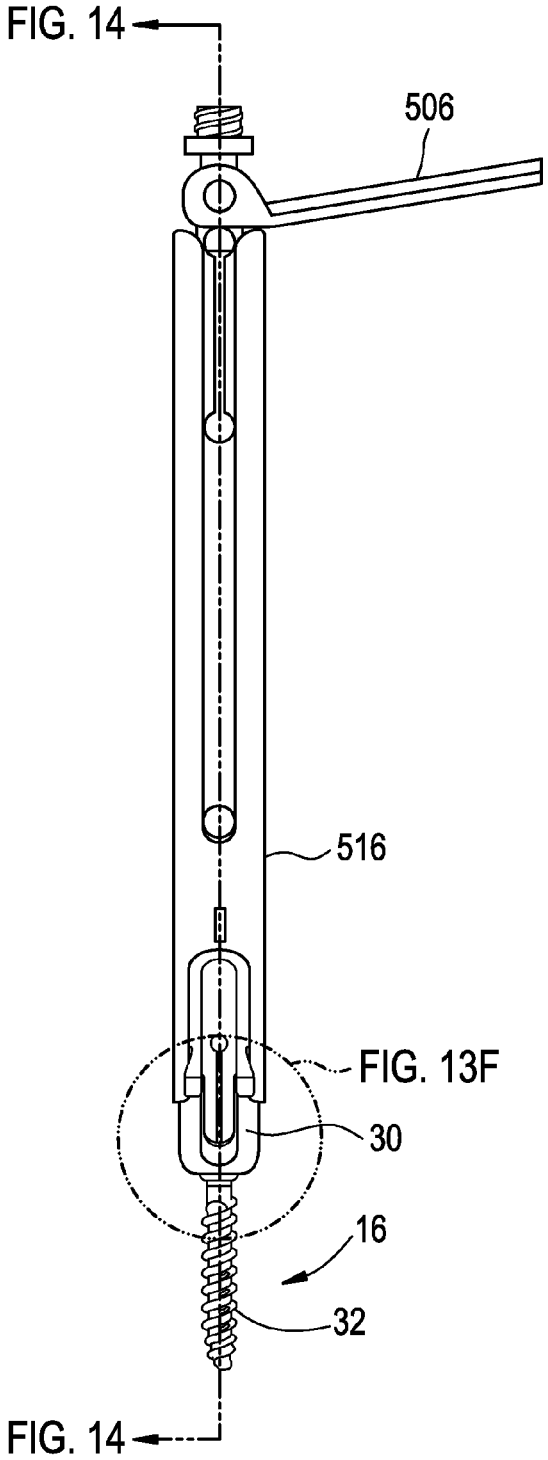
Figure 14:
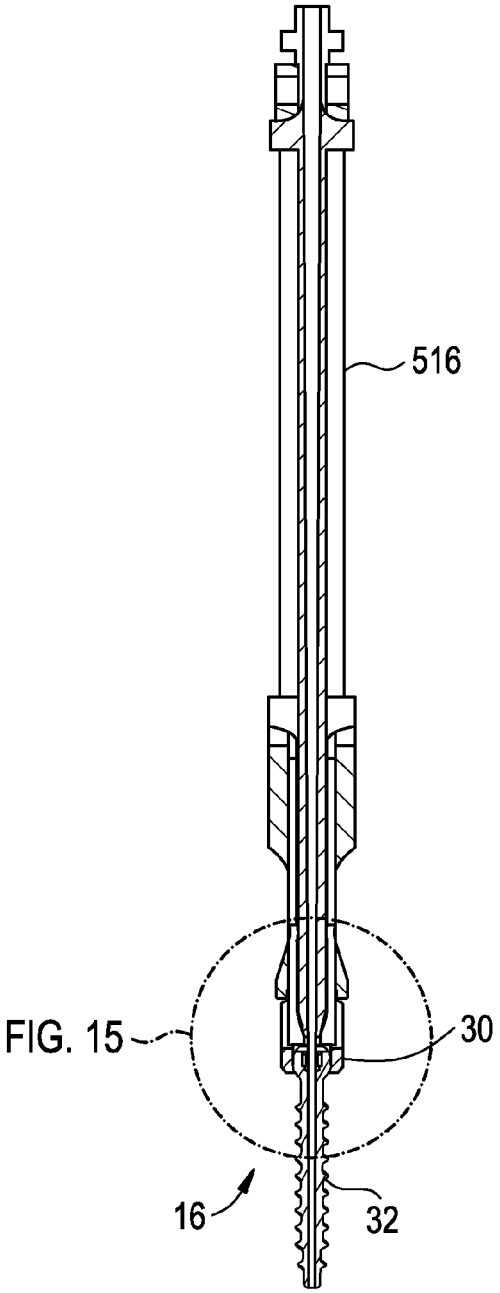
FIG. 14 is a side view in cross section of the system of FIGS. 13A-E, illustrating the anchor connection instrument connected to the bone anchor 16.
Figure 13F:
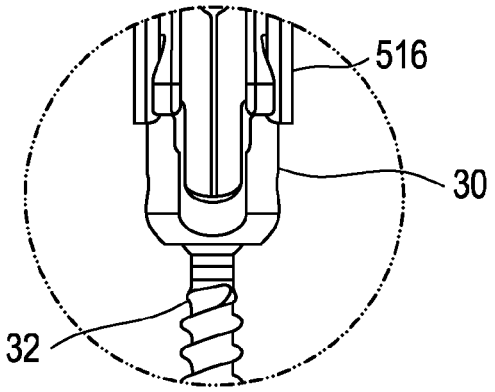
Figure 15:
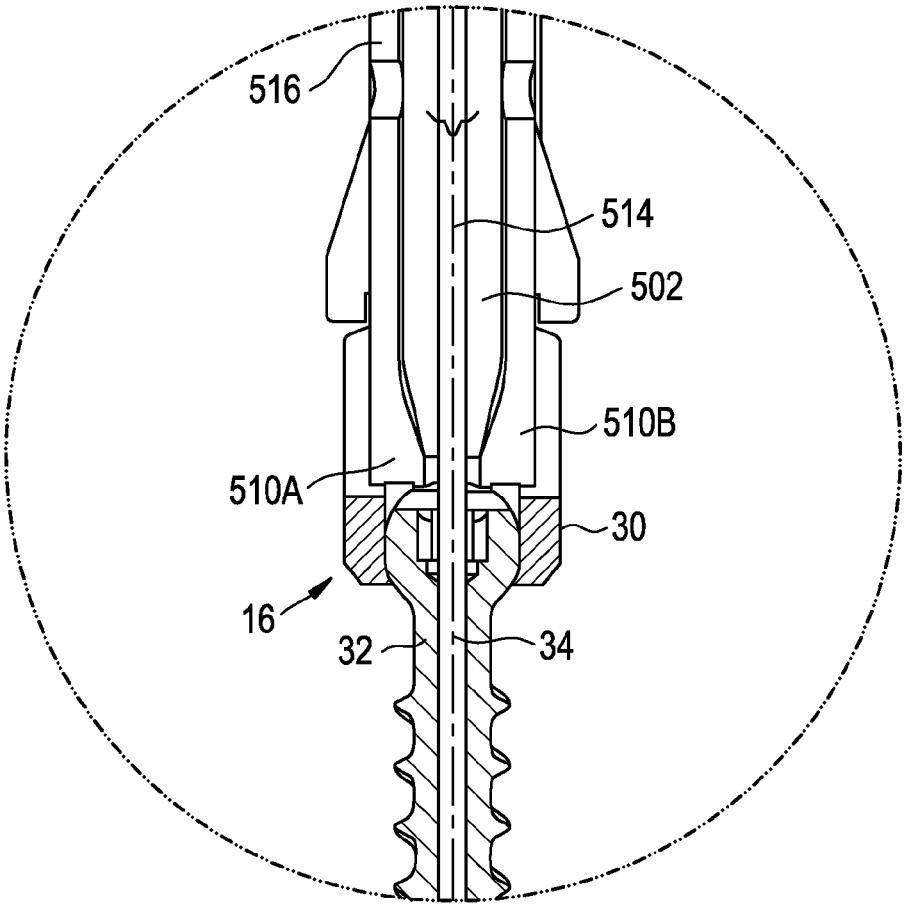
FIG. 15 is a side view in cross section of the distal end of the anchor connection instrument of FIG. 14.

FIGS. 12A-12C illustrate another exemplary embodiment of a system for delivering bone cement or other materials to a bone anchor. In the exemplary system, the cement delivery tube 14 may be connected to bone anchor 16 with an anchor connection instrument 400 configured to engage the interior of the proximal portion 30 of the bone anchor 16. The exemplary anchor connection instrument 400 is analogous in construction and use to the anchor connection instrument 300 described above except the anchor connection instrument 400 has a single prong 408 rather two prongs 308A, 308B. In addition, the distal end 404 of the anchor connection instrument 400 is shaped to fit within the rod slot 31 of the bone anchor 16. For example, the distal end 404 of the instrument 400 is generally T-shaped having a pair of opposed extensions 420A, 420B that extend from the instrument and that each have an arcuate lower surface for engaging the arcuate surface on the proximal portion 30 of the bone anchor 16 that bounds the rod slot 31. The extensions 420A, 420B, when positioned in the rod slot 31 of the bone anchor 16, provide stability and limit rotation of the anchor connection instrument 400 relative to the bone anchor 16. The anchor connection instrument 300 described above in connection with FIGS. 11A and 11B may also be provided with extensions analogous to extensions 420A, 420B.

FIGS. 13A-15 illustrate an another exemplary embodiment of a system for delivering bone cement or other materials to a bone anchor. In the exemplary system, a cement delivery tube 514 may be connected to bone anchor 16 with an anchor connection instrument 500 configured to engage the interior of the proximal portion 30 of the bone anchor 16 through a screw extension connected 516 to the bone anchor 16. The exemplary screw extension 516 is used to percutaneously place a bone anchor, such as bone anchor 16, and to delivery a spinal rod to the bone anchor and other bone anchors in a minimally invasive procedure. Exemplary screw extensions are available in the VIPER and VIPER II Spinal Fixation Systems available from DePuy Spine of Raynham, Mass., and are described in U.S. Patent Application Publication Nos. US 2005/0131408 and US 2005/0131421, each of which is incorporated herein by reference. The exemplary anchor connection instrument 500 is sized to fit within the exemplary screw extension 516, e.g., having an external diameter less than the inner diameter of the screw extension.

The anchor connection instrument 500 includes an inner longitudinally adjustable member 502 that receives the cement delivery tube 514 and an outer sleeve 504 positioned about the inner member 502. A handle 506 is connected to the inner member 504. The inner member 502 may be adjusted between a proximal position and a distal position relative to the outer sleeve 504. The outer sleeve 504 has a distal end 508 having two laterally adjustable prongs 510A, 510B. Advancement of the inner member 502 relative to the outer sleeve 504 from the proximal position to the distal position causes the prongs 510A, 510B to move laterally, in a direction transverse to the longitudinal axis, which facilitates engagement with bone anchor. For example, the prongs 510A, 510B may enter the rod slot 31 in the proximal portion 33 of the bone anchor thereby connecting the outer sleeve 508, and the cement delivery tube 514 to the bone anchor 30. Handle 506 may be rotated to effect movement of the inner member between the proximal position to the distal position.

Figure 16A:
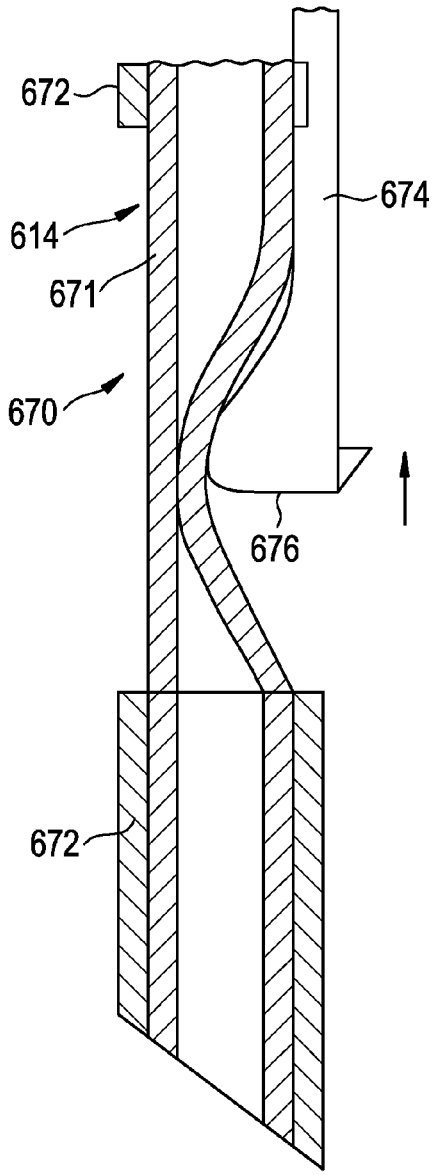
FIGS. 16A-16B are side views in cross section of an exemplary bone cement delivery tube including a valve at a distal end thereof, illustrating the valve in an open and a closed position.
Figure 16B:
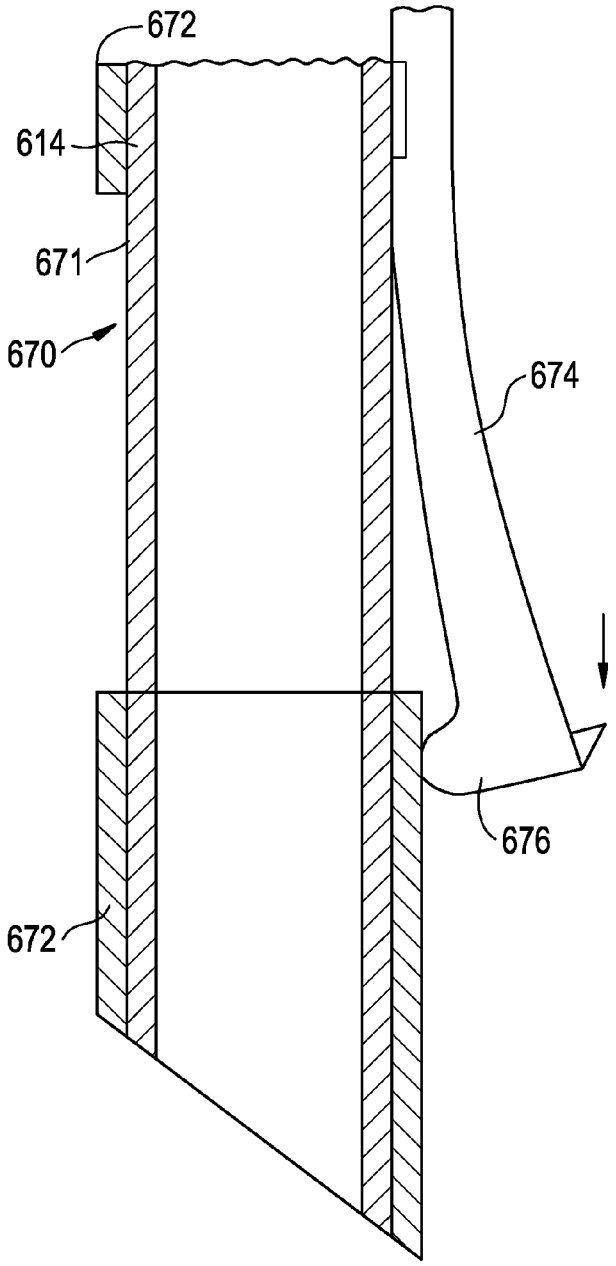

FIGS. 16A and B illustrate another exemplary embodiment of a cement delivery tube 614 that includes an integral valve at the distal end of the cement delivery tube. The exemplary cement delivery tube 614 includes a compressible section 670 in which a portion of the wall of the tube 614 may be compressed to selectively interrupt flow of cement through the cement delivery tube 14. In one embodiment, for example, the cement delivery tube 14 may include an inner tube 671 constructed from a resilient compressible material, such as a polymer, and may be selectively encased or enclosed by a coaxial sleeve 672 of a rigid material, such as a rigid polymer or a metal. A section of the length of the inner tube 671 may be exposed, e.g., not enclosed, to provide the compressible section 670 which may operate as a valve. The compressible section 670 may be provided at any point along the length of the tube 614.

The anchor connection instrument or other instrument may be used to selectively compress the wall of the inner tube 671 at the compressible section 670 to obstruct the inner tube 671. For example, the anchor connection instrument may include a longitudinally adjustable valve member 674 that includes a projection 676 or the like for compressing the wall of the inner tube 671 at the compressible section 670. The valve member 674 may be a prong, analogous to the prongs 308A, B and 408, described above, and may also be used to engage the instrument to the bone anchor. In the exemplary embodiment, when the valve member 674 is in a proximal position, the projection 676 compresses the wall of the inner tube 671 to obstruct the inner tube 671. In a distal position, the projection 676 abuts the rigid out sleeve 672 and the inner tube remains unobstructed.

FIGS. 17A-17E illustrate another exemplary embodiment of a system for delivering bone cement or other material to a bone anchor. The exemplary system includes an anchor connection instrument 600 including an instrument body 601 having a proximal end 602 for connection to a cement delivery tube, such as, for example, cement delivery tube 14 or cement delivery tube 614, described below, a distal end 604 sized and shaped to fit within the proximal portion 30 of the bone anchor 16, and passage 606 between the proximal end 602 and the distal end 604 through which the cement delivery tube may be positioned to connect to the passage 34 in the bone anchor 16.

Figure 17A:
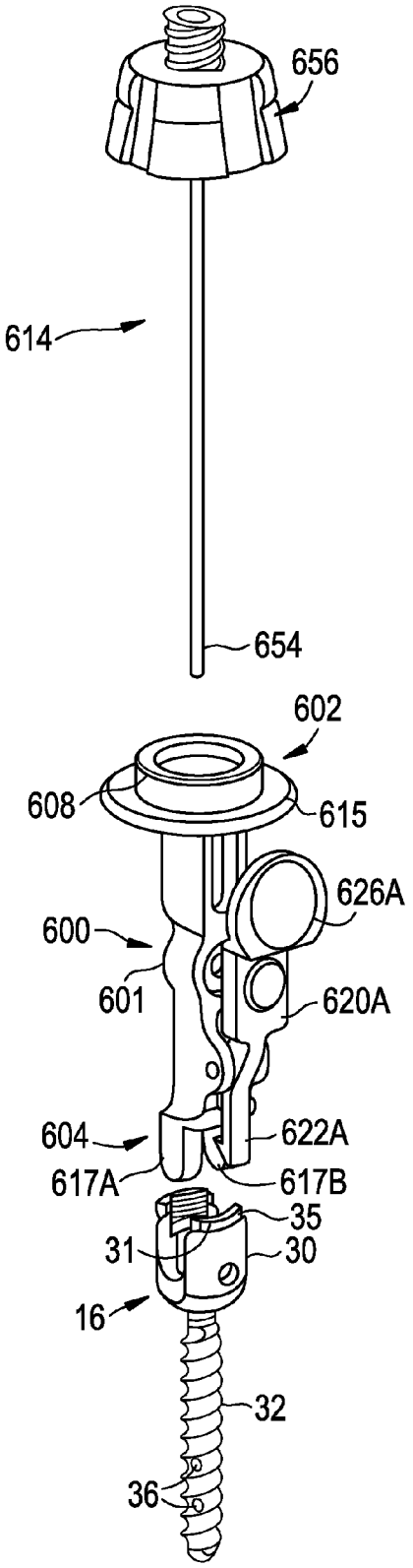
FIG. 17A is an exploded view of another exemplary system for delivering bone cement to a bone anchor, illustrating the anchor connection instrument and the cement delivery tube of the system and a bone anchor.
Figure 17B:
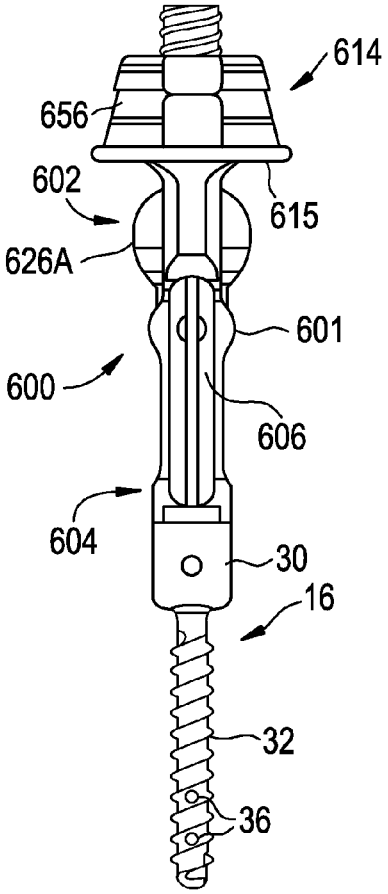
FIG. 17B is a front view of the system of FIG. 17A, illustrating the anchor connection instrument and the cement delivery tube of the system connected to the bone anchor.
Figure 17C:
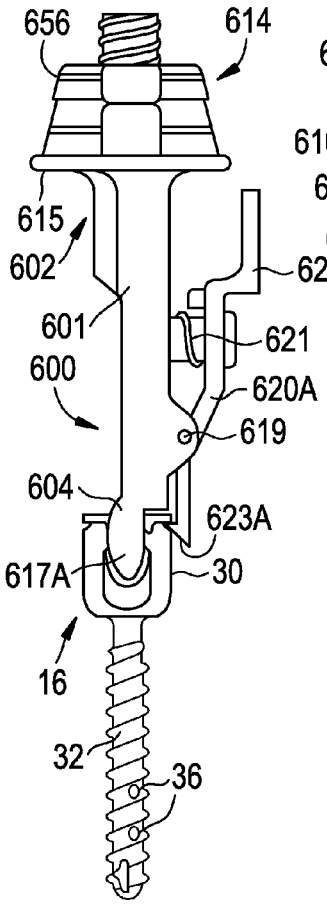
FIG. 17C is a side view of the system of FIG. 17A, illustrating the anchor connection instrument and the cement delivery tube of the system connected to the bone anchor.
Figure 17D:
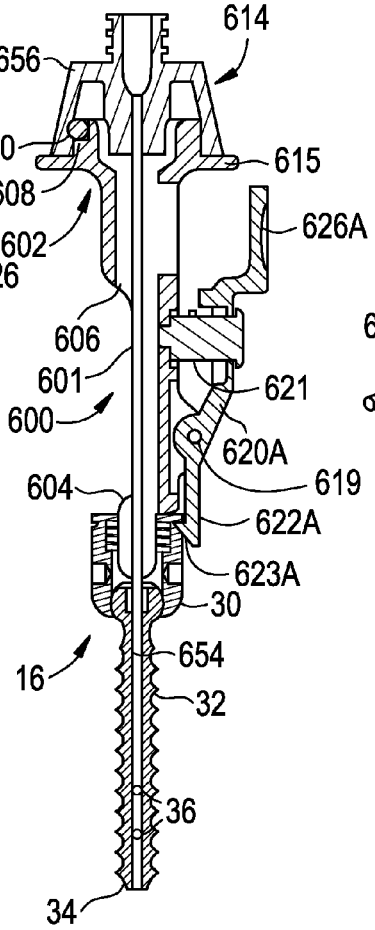
FIG. 17D is a side view in cross section of the system of FIG. 17A, illustrating the anchor connection instrument and the cement delivery tube of the system connected to the bone anchor.
Figure 17E:
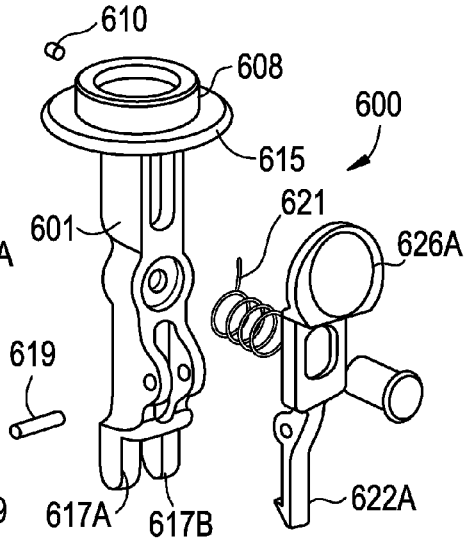
FIG. 17E is an exploded view of the anchor connection instrument of the system of FIG. 17A.

The proximal end 602 of the exemplary instrument body 601 may include an annular collar 608 defining an opening to the passage 606 of the instrument 600. The collar 608 may include a connection feature to facilitate connection to the proximal end of the cement delivery tube. The connection feature may be an external thread, an internal thread, a groove or opening for receiving a projection or the like, or other known connection features. Alternatively, the collar 608 may connect to the proximal end of the tube by a simple friction fit. In the illustrated embodiment, the collar 608 includes a single pin 610 extending from the outer surface of the collar 608 that engages an internal thread provided on the proximal end 656 of the tube 614. The proximal end 602 of the instrument body 601 further includes a flange 615 having an outer diameter greater than the outer diameter of the collar 608. The proximal end 656 of the tube 614 may be advanced into contact with the flange 615, as illustrated in FIGS. 17B-D.

The distal end 604 of the anchor connection instrument 600 includes two spaced-apart arms 617A, 617B that are sized and shaped to fit within the rod receiving slot 31 of the bone anchor 16. For example, the distal end of the arms 617A, 617B are generally arcuate in shape having a curvature approximating the curvature of the rod contacting surfaces of the rod receiving slot 31.

The exemplary anchor connection instrument 600 further includes a first member 620A that is adjustable relative to the instrument body 601 of the instrument 600. For example, the first member 620A may be pivotally connected to the instrument body 601 and may be pivotable between a release position, in which the distal end 622A of the first member 620A is pivoted away from the instrument body to facilitate removal of the instrument 600 from the proximal end 30 of the bone anchor, and a connect position in which the distal end 622A of the first member 620A is pivoted toward the instrument body and the distal end 622A can engage the proximal end 30 of the bone anchor 16 to connect the instrument 600 to the bone anchor 16. The first member 620A is connected to the instrument body 601 by a pivot pin 619 positioned between the proximal handle 626A of the first member 620A and the distal end 622A of the first member 622A. A spring 621 or other biasing mechanism may be interposed between the instrument body 601 and the first member 620A to bias the first member 620A to the connect position. The distal end 622A of the first member 620A includes a ramped surface 623A that is effective to pivot the distal end 622A away from the instrument body 601, toward the release position, as the distal end 622A is advanced distally into engagement with the proximal end 30 of the bone anchor 16. The distal end 622A may include a feature, such as a projection, for engaging one of the slots 35 provided on the proximal end 30 of the bone anchor 16. In the exemplary embodiment, the proximal terminus of the ramped surface 623A engages one of the slots 35 provided on the proximal end 30 of the bone anchor 16. In alternative embodiments, the instrument 600 may include a second member, analogous in construction to the first member 620A, pivotally connected to the instrument body 601 at a location diametrically opposed to the first member 620A for engaging a second one of the slots 35 on the bone anchor 16.

The proximal end 656 of the cement delivery tube 614 is generally annular in shape and includes an internal thread for engaging the pin 610 provided on the collar 608 of the instrument body. The proximal end 656 thus may be rotated into and out of engagement with the collar 608 of the instrument body 601 to thereby connect the tube 614 to the instrument 600 and position the distal end 654 of the tube 614 within the channel 34 of the bone anchor 16. The proximal end 656 of the tube 614 may also include a luer lock connector or other connector to connect the tube 614 to the cement delivery system 18.

In use, the cement delivery tube 614 may be connected to the anchor connection instrument 600. The instrument 600 may be connected to a bone anchor 16 by advancing the arms 617A, 617B into the rod receiving slot 31 of the proximal end 30 of the bone anchor 16. During this advancement, the ramped surface 623A of the distal end 622A of the first member 620A engages the outer surface of the proximal end 30 of the bone anchor 16 causing the first member 620A to pivot from the connect position toward the release position against the spring force provided by spring 621. When the arms 617A, 617B are seated in the rod receiving slot, the proximal terminus of the ramped surface 623A snaps into the groove 35 to thereby connect the anchor connection instrument 600 and the cement delivery tube 614 to the bone anchor 16. Cement from the cement delivery system 18 may then be provided to the bone anchor 16 through the tube 614.

In procedures in which multiple bone anchors are employed, a plurality of anchor connection instruments, including anchor connection instrument 600, may be connected to some or all of the bone anchors. A single cement delivery tube, such as a cement delivery tube 614, may be used to provide a connection to the cement delivery system 18 and deliver cement to the plurality of bone anchors. For example, the cement delivery tube 614 may be connected to a first anchor connection instrument 600 connected to a first bone anchor and cement delivered to the first bone anchor. The cement delivery tube 614 may be disconnected from the first anchor connection instrument, while remaining connected to the cement delivery system 18, and connected to a second anchor connection instrument connected to a second bone anchor. Once the desired amount of cement is delivered to the second bone anchor, the cement delivery tube 614 may be disconnected from the second anchor connection instrument 600 and the above process may be repeated for other anchor connection instruments connected to the other bone anchors. Thus, a system for delivering cement to a plurality of bone anchors may include a plurality of anchor connection instruments 600 and a cement delivery tube 614 connectable to each of the plurality of anchor connection instruments 600.

Alternatively, the anchor connection instrument 600 and the cement delivery tube 614 can be collectively connected and disconnected as a single unit from a plurality of bone anchors in the manner described above in connection instrument 12 and tube 14.

Figure 18A:
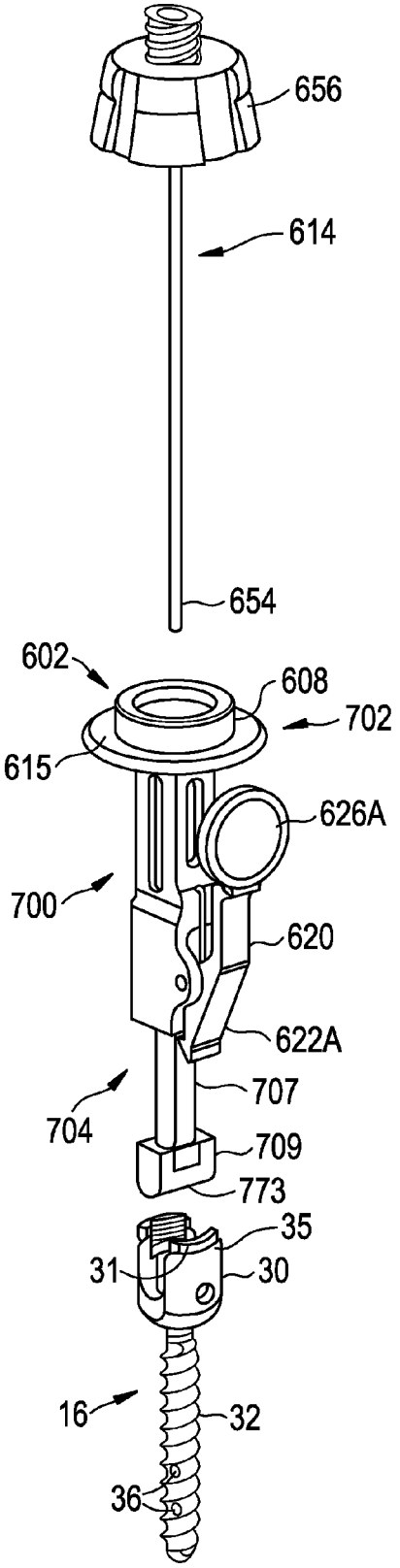
FIG. 18A is an exploded view of another exemplary system for delivering bone cement to a bone anchor, illustrating the anchor connection instrument and the cement delivery tube of the system and a bone anchor.
Figure 18B:
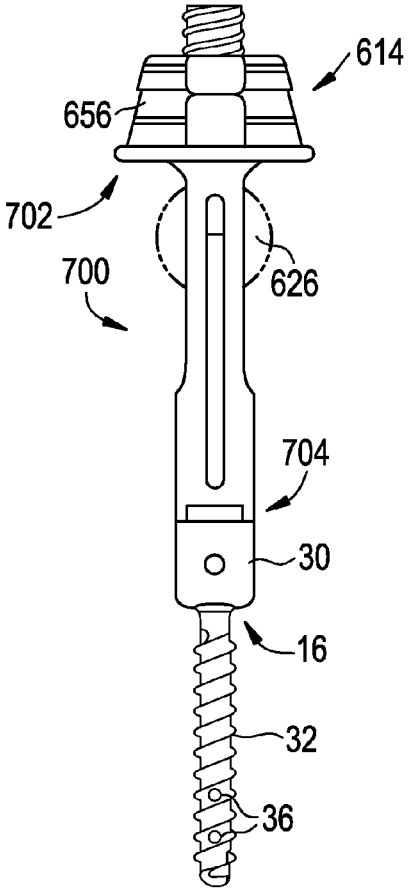
FIG. 18B is a front view of the system of FIG. 18A, illustrating the anchor connection instrument and the cement delivery tube of the system connected to the bone anchor.
Figure 18C:
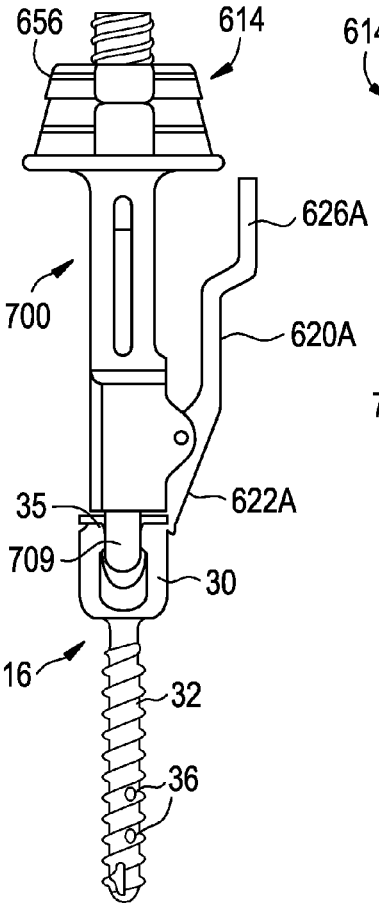
FIG. 18C is a side view of the system of FIG. 18A, illustrating the anchor connection instrument and the cement delivery tube of the system connected to the bone anchor.
Figure 18D:
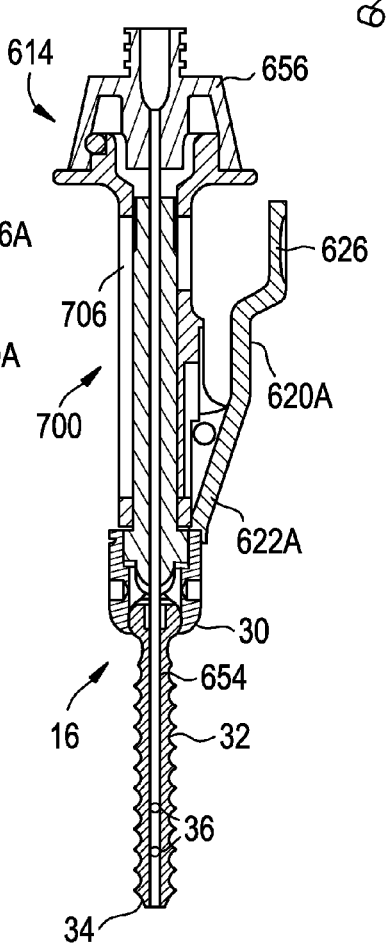
FIG. 18D is a side view in cross section of the system of FIG. 18A, illustrating the anchor connection instrument and the cement delivery tube of the system connected to the bone anchor.
Figure 18E:
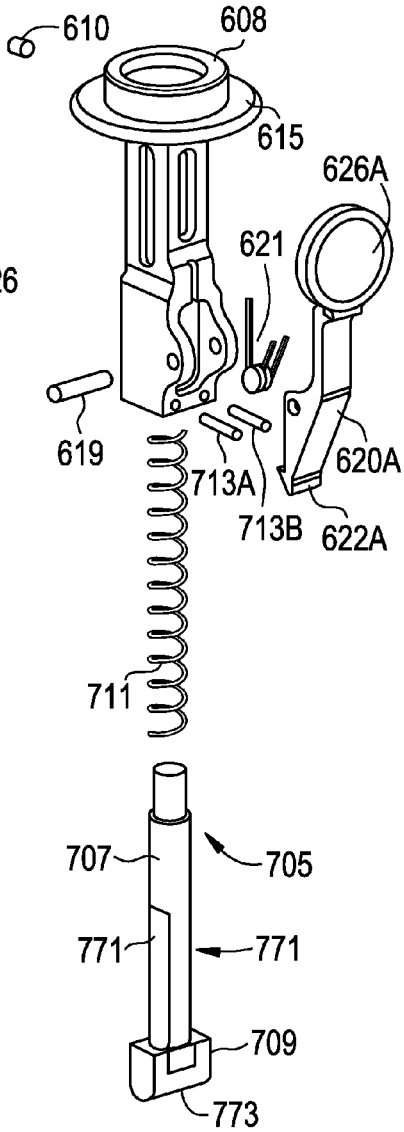
FIG. 18E is an exploded view of the anchor connection instrument of the system of FIG. 18A.

FIGS. 18A-18E illustrate another exemplary embodiment of a system for delivering bone cement or other material to a bone anchor. The exemplary system includes an anchor connection instrument 700 that is analogous in construction to the anchor connection instrument 600 described above except that the distal end 704 of the instrument body 701 includes a connection member 705 that is longitudinally adjustable relative to the instrument body 701. In the exemplary instrument 700, the distal end 704 of the instrument body 701 includes floating connection member 705 having a generally cylindrical body 707 and an enlarged distal end 709 configured to be seated in the rod receiving slot 31 of the proximal end 30 of the bone anchor 16. The connection member 705 is positioned within the central passage 706 of the instrument body 701 and movable along the length of the central passage 706 relative to the instrument body 701 between an extended position in which the distal end 709 of the connection member 705 is extended distally away from the instrument body 701 and a retracted position in which the distal end 709 of the connection member 705 is positioned proximate the instrument body. FIG. 18A illustrates the connection member 705 in the extended position. FIGS. 18B-D illustrate the connection member 705 in the retracted position. A spring 711 or other biasing member may be provided to bias the connection member 705 into the extended position. The connection member 705 and the instrument body 701 may include a retaining feature to inhibit separation of the connection member 705 from the instrument body 701. For example, the instrument body 701 may include one or more projections, e.g. pins 713A, B, that project into the central passage 706 of the instrument body 701 and engage the connection member 705. For example, the pins 713 A, 713B may be seated in longitudinal slots 771 provided on diametrically opposed locations of the connection member 705.

The enlarged distal end 709 of the connection member 705 may have an arcuate contact surface 773 sized to span the length of the rod receiving slot 31 of the bone anchor 16. The arcuate contact surface 773 may have a curvature that is approximately equal to the curvature of the rod contacting surfaces of the rod receiving slot 31 of the proximal end 30 of the bone anchor 16. In addition, the arcuate contact surface 773 may have a curvature that is approximately equal to the curvature of the rod to be positioned within the rod receiving slot 31 of the proximal end 30 of the bone anchor 16.

In use, the instrument 700 may be connected to the bone anchor 12 by positioning the connection member 705 of the instrument 700, in the extended position, into the rod receiving slot 31 of the proximal end 30 of the bone anchor 16, as illustrated in FIG. 18A. Preferably, the cement delivery tube 614 is connected to the instrument 700 prior to connecting the instrument 700 to the bone anchor 16. The distal end 654 of the cement delivery tube 614 is positioned within the connection member 705 such that only a portion of the distal end 654 if the tube 614 extends beyond the arcuate contact surface 773. The connection member 705 thereby serves to shield the tube 614 during the connection process while concomitantly permitting adjustment of the proximal end 30 of the bone anchor 16 relative to the bone engaging portion 32 of the bone anchor 16. This adjustability facilitates alignment of the distal end 654 of the tube 614 with the passage 34 of the bone anchor 16. As the connection instrument 700 is advanced distally relative to the bone anchor 16 to connect to the bone anchor 16, the connection member 705 is adjusted to the retracted position thereby exposing more of the tube 614 for insertion into the passage 34 of the bone anchor 16.

FIGS. 19A-19E illustrate another exemplary embodiment of a system for delivering bone cement or other material to a bone anchor. In the exemplary system, an anchor connection instrument 700 is configured to be positioned through a tubular screw extension connected to the bone anchor 16. The screw extension may be a minimally invasive screw extension such as the open screw extension 516 described above in connection with FIGS. 13A-15, or may be the closed minimally invasive screw extension 517 illustrated in FIGS. 19A-19E. The minimally invasive screw extension may be connected to the bone anchor 30 and may be used to percutaneously place a bone anchor, such as bone anchor 16, over a guide wire in a minimally invasive procedure.

The exemplary anchor connection instrument 800 includes a generally tubular instrument body 802 having a proximal end 806 for connection to the proximal end of a cement delivery tube, such as the proximal end 856 of the cement delivery tube 814, a distal end 804 configured to connect to a bone anchor, such as bone anchor 30, and a central passage spanning from the proximal end 806 to the distal end 804 through which the cement delivery tube may be delivered to the bone anchor. The proximal end 806 of the instrument 800 may include an annular collar 808 having an annular side wall spaced apart from the outer wall of the tubular instrument body 802. The annular collar 808 may be positioned about the screw extension and optionally may include a connection feature, such as a projection or a groove, to connect with a mating connection feature on the proximal end of the screw extension 517. The proximal end 806 may also include a connection feature to permit the proximal end of the cement delivery tube to be connected to the instrument 800. In the exemplary embodiment, for example, the proximal end 806 of the instrument body 802 includes an annular groove 809 for receiving the prongs 882A, 882B of the proximal end 856 of the cement delivery tube 814.

The distal end 804 of the instrument body 802 may include a first connection feature for connecting to the proximal end 30 of the bone anchor 16 and a second connection feature to connect with the bone engaging portion 32 of the bone anchor 16. The first connection feature 810, in the exemplary embodiment, is an externally threaded section 810 that threadingly engages the internal thread 33 provided on the proximal portion 30 of the bone anchor 16 to receive a closure mechanism. The second connection feature is a drive tip 812 that engages the drive feature provided on the proximal head of the bone engaging portion 32 to permit the bone engaging portion 32 to be anchored into bone. The first connection feature and the second connection feature permit the instrument 800 to hold the proximal rod receiving portion 30 of the bone anchor 16 relative to the bone engaging portion 32 of the bone anchor 16 which allows the distal tip 854 of the cement delivery tube 814 to be more easily placed in the passage 34 of the bone anchor 16.

The exemplary cement delivery tube 814 includes a proximal end 856 configured to connect to the proximal end 806 of the instrument 800 and to the cement delivery system 18 and a distal end [865] *854* sized to be positioned within the passage 34 of the bone anchor 16 and deliver cement from the cement delivery system 18 to the bone anchor 16. The proximal end 856 includes a connection feature for connecting to a mating connection feature on the proximal end 806 of the instrument 800. For example, the proximal end 856 of the exemplary tube 814 includes two spaced-apart flexible, resilient prongs 882A, 882B that may be snapped into the groove 809 on the proximal end 806 of the instrument 800. The proximal ends 884A, 884B of the prongs 882A, 882B may be compressed together to release the distal ends 886A, 886B of the prongs from the groove 809. In addition, the tube 814 may include a connection feature, such as a [leur] *luer* lock connector, to connect the tube 814 to the cement delivery system 18.

Figure 19A:
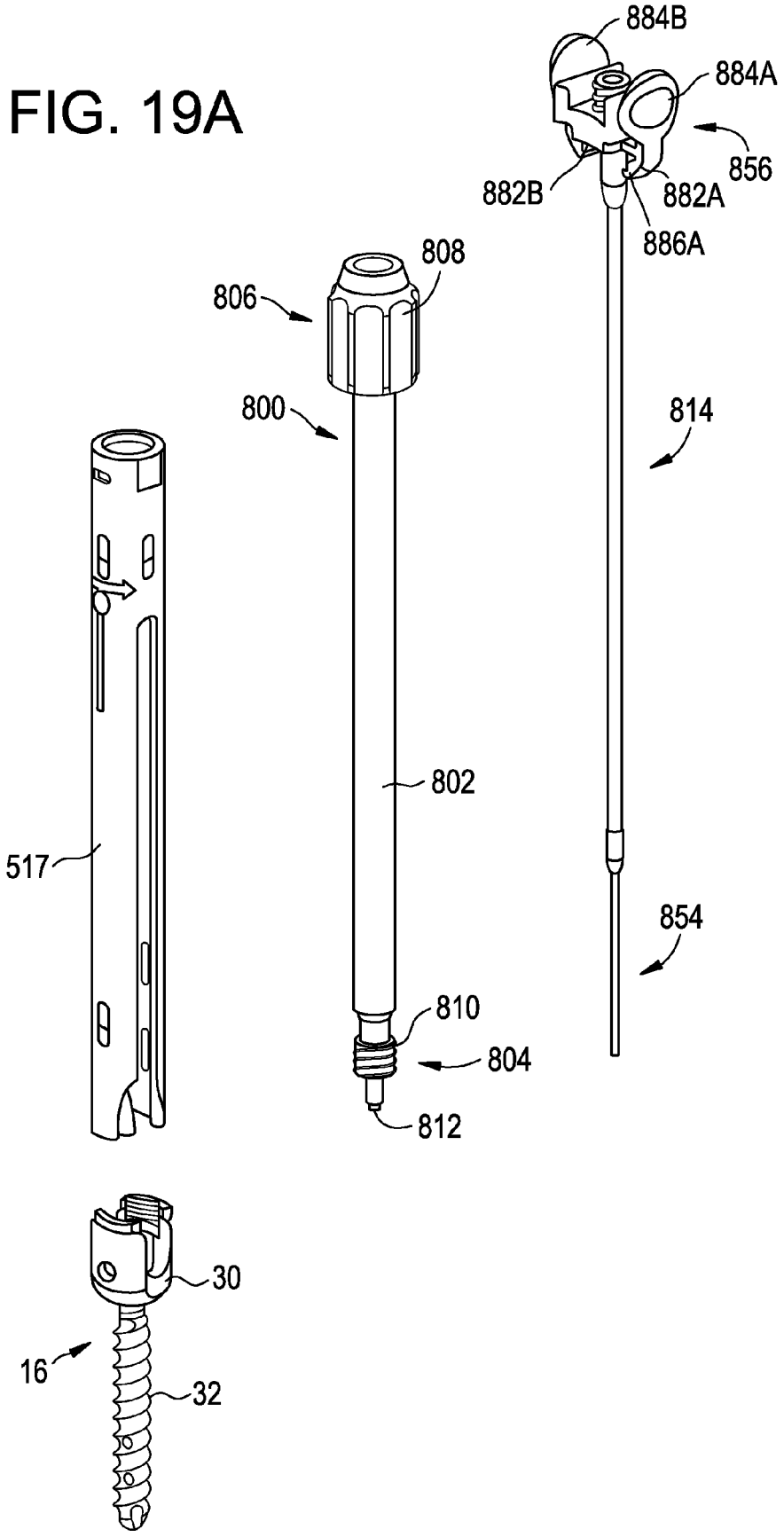
FIG. 19A is an exploded view of another exemplary system for delivering bone cement to a bone anchor, illustrating the anchor connection instrument and the cement delivery tube of the system and a screw extension and a bone anchor.
Figure 19B:
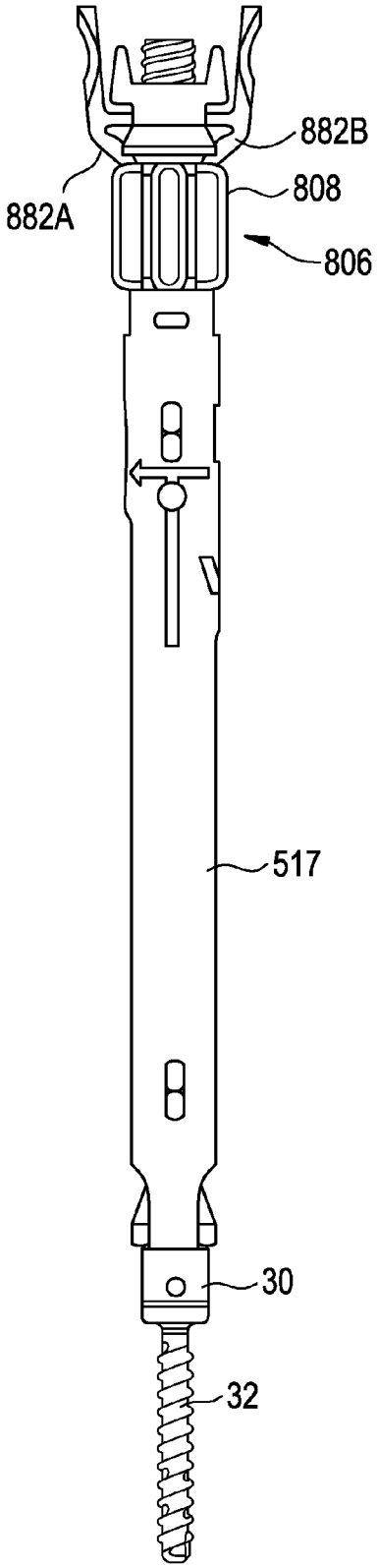
FIG. 19B is a side view of the system of FIG. 19A, illustrating the anchor connection instrument and the cement delivery tube of the system connected to the screw extension and the bone anchor.
Figure 19C:
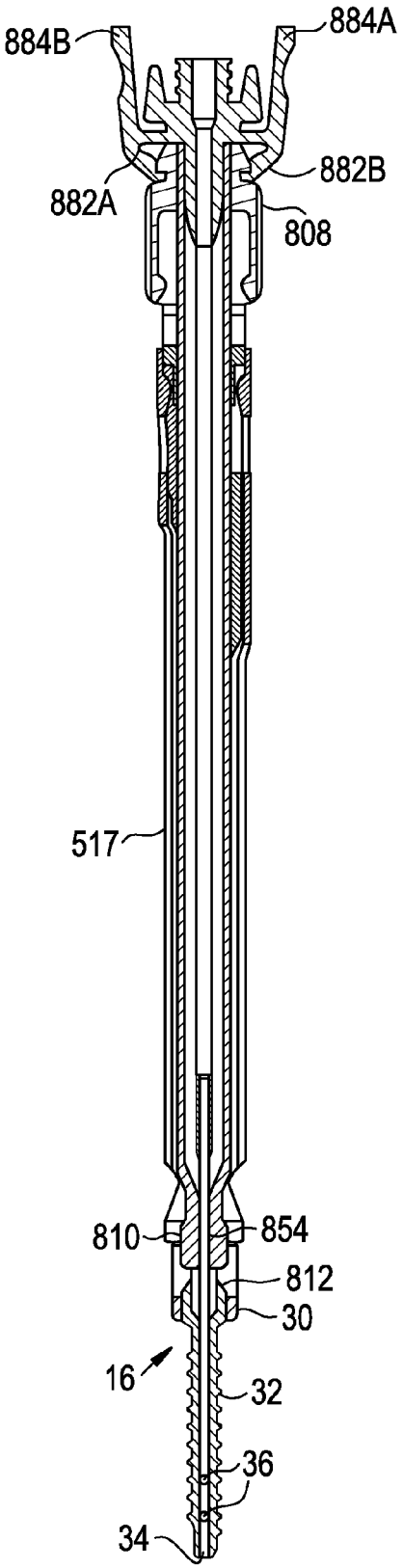
FIG. 19C is a side view in cross section of the system of FIG. 19A, illustrating the anchor connection instrument and the cement delivery tube of the system connected to the screw extension and the bone anchor.
Figure 19D:
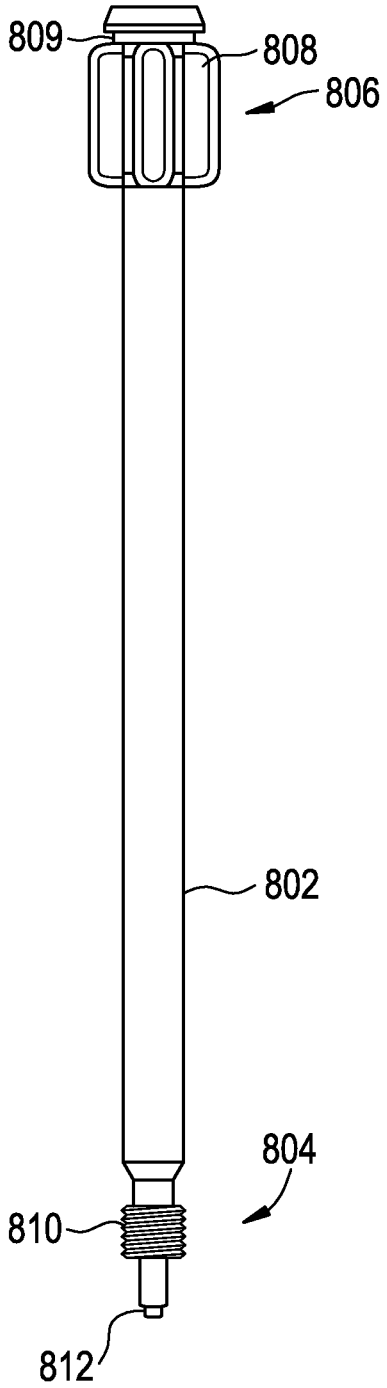
FIG. 19D is side view of the anchor connection instrument of the system of FIG. 19A.
Figure 19E:
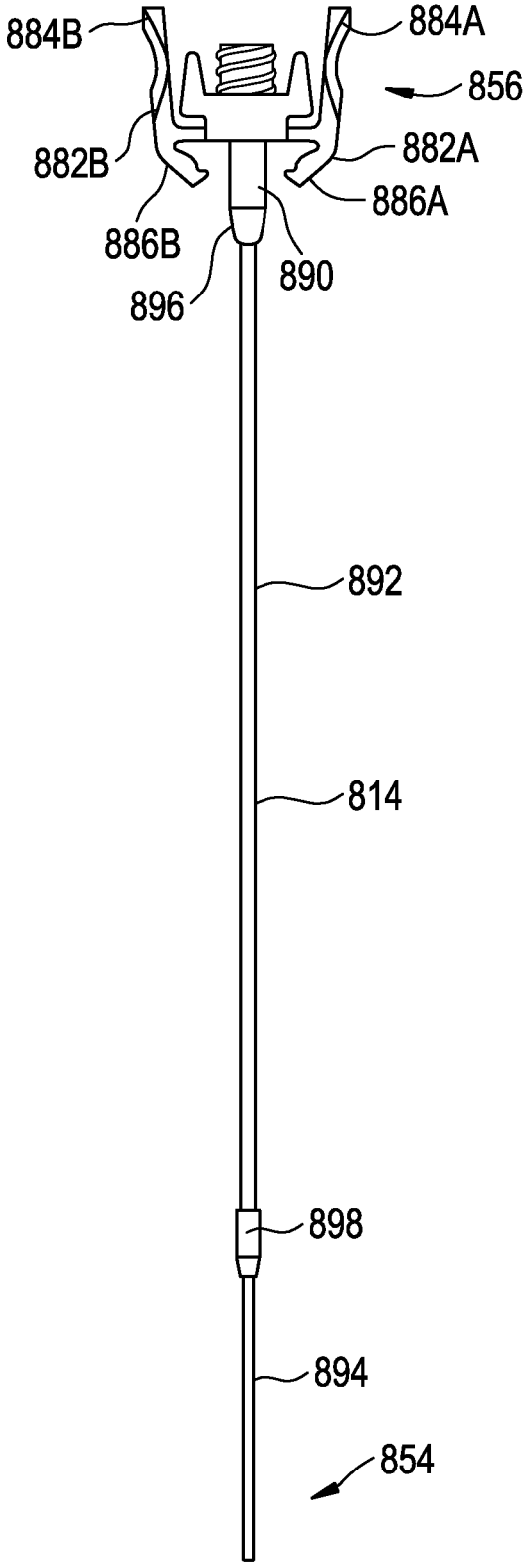
FIG. 19E is side view of the cement delivery tube of the system of FIG. 19A.
Figure 20A:
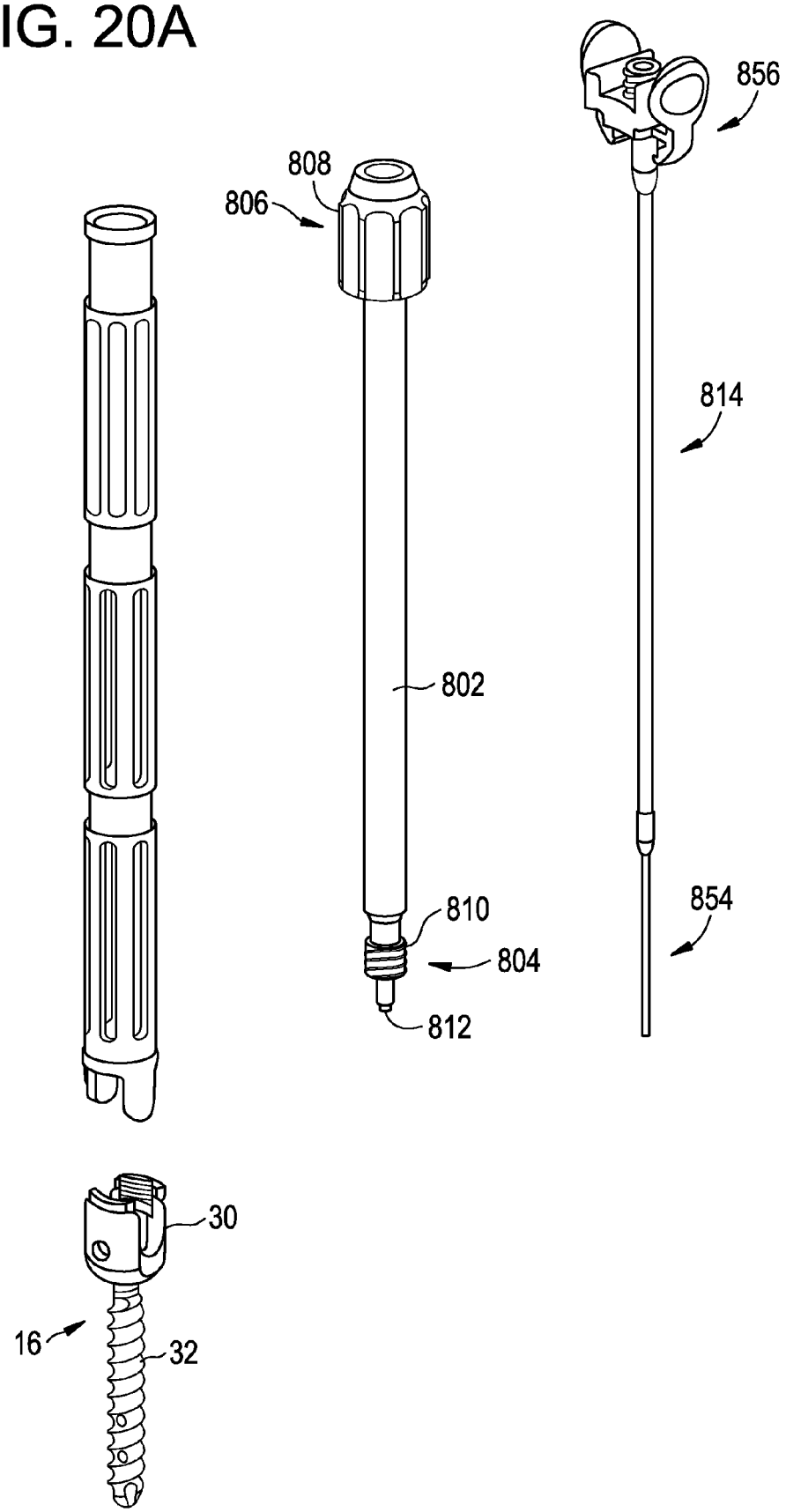
FIG. 20A is an exploded view of another exemplary system for delivering bone cement to a bone anchor, illustrating the anchor connection instrument, the cement delivery tube, and the counter-torque instrument of the system and a bone anchor.
Figure 20B:
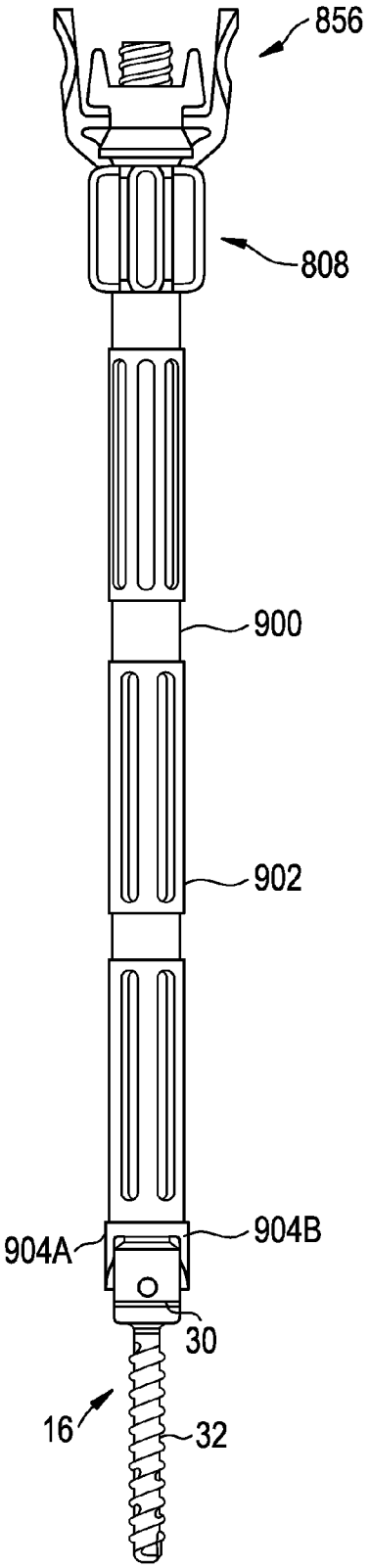
FIG. 20B is a side view of the system of FIG. 20A, illustrating the anchor connection instrument, the cement delivery tube, and the counter-torque instrument of the system connected to the bone anchor.
Figure 20C:
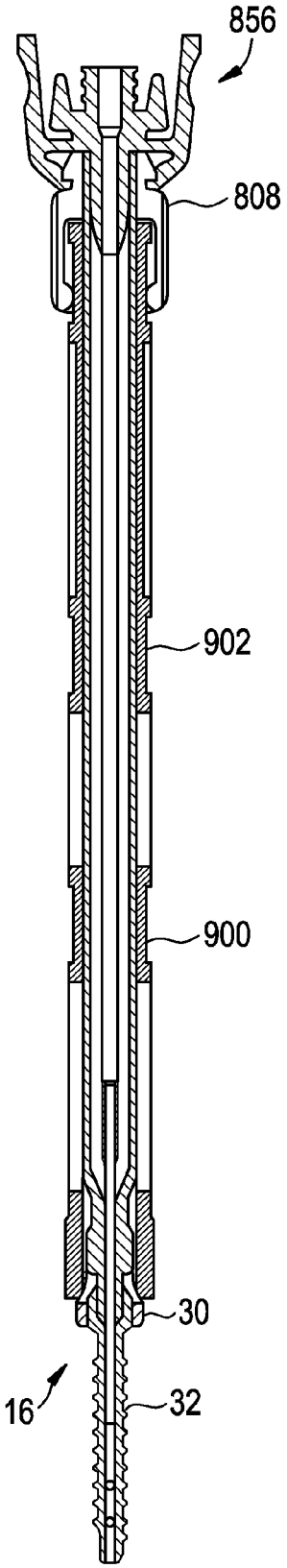
FIG. 20C is a side view in cross section of the system of FIG. 20A, illustrating the anchor connection instrument, the cement delivery tube, and the counter-torque instrument of the system connected to the bone anchor.
Figure 20D:
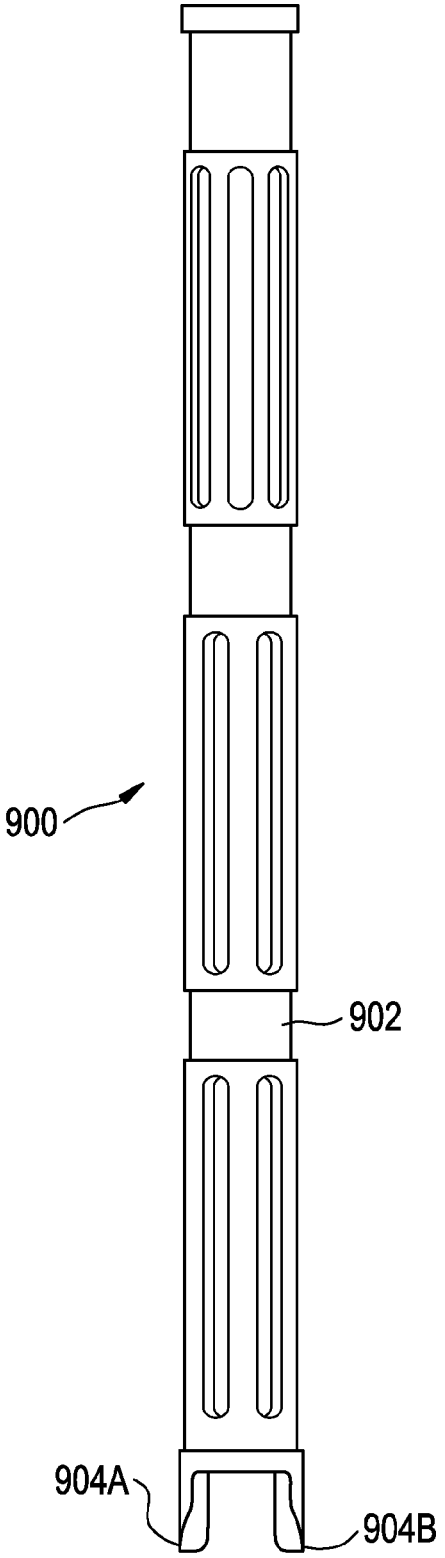
FIG. 20D is front view of the counter-torque instrument of the system of FIG. 20A.
Figure 20E:
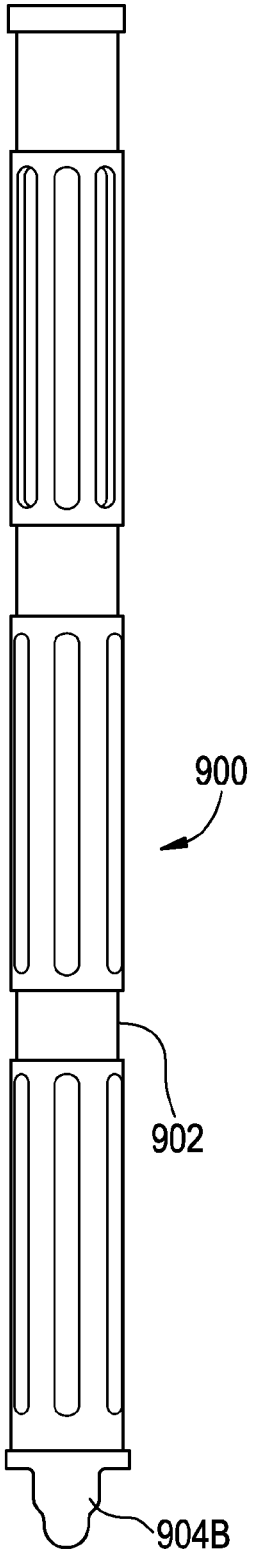
FIG. 20E is side view of the counter-instrument of the system of FIG. 20A.

Referring to FIG. 19E, the cement delivery tube 814 may taper from an increased inner diameter at the proximal end to 856 a reduced diameter at the distal end 854 to maximize the flow of cement within the tube 814 and thereby extend the working time of the cement. In the exemplary embodiment, for example, the tube 814 includes a first section 890, a second section 892 distal to the first section 890, and a third section 894 distal to the second section 892. The first section 890 has a first inner diameter that is greater than the second inner diameter of the second section 892, which is greater than the third inner diameter of the third section 894. A first tapering section 896 interposed between the first section 890 and the second section 892 provides a tapering inner diameter from the first diameter to the second diameter. A second tapering section 898 interposed between the second section 892 and the third section 894 provides a tapering inner diameter from the second diameter to the third diameter. Any number of different diameter sections may be provided. Alternatively, the inner diameter of the tube may taper continuously from a diameter at the proximal end 856 to a second diameter at the distal end 854.

The exemplary anchor connection instrument 800 and the cement delivery tube 814 may also be used in open procedures or procedures in which a screw extension is not connected to the bone anchor. Referring to FIGS. 20A-E, for example, the exemplary instrument 800 and the cement delivery tube 814 may be used in connection with a counter-torque instrument 900 which allows the distal end 804 of the instrument 800 to be rotated into engagement with the proximal end 30 of the bone anchor 16. The counter-torque instrument 900 includes a generally tubular body 902 having a central passage through which the connection instrument 800 and the cement delivery tube 814 may be positioned. The body 902 of the instrument 900 may include a number of slots or openings therein to reduce the weight of the instrument 900 and to facilitate cleaning of the instrument. The distal end 904 of may include two spaced apart, diametrically opposed fingers 904A, 904B for positioning within the rod receiving slot 31 of the bone anchor 16.

In use, fingers 904A, 904B of the counter-torque instrument 900 are positioned within the rod receiving slot 31 of the bone anchor 16 during rotational engagement and disengagement of the externally threaded section 810 of the anchor engagement instrument 800 with the internal thread 33 provided on the proximal portion 30 of the bone anchor 16. The counter-torque instrument 900 prevents rotation of the proximal end 30 of the bone anchor 16 relative to the anchor connection instrument 800.

Figure 21:
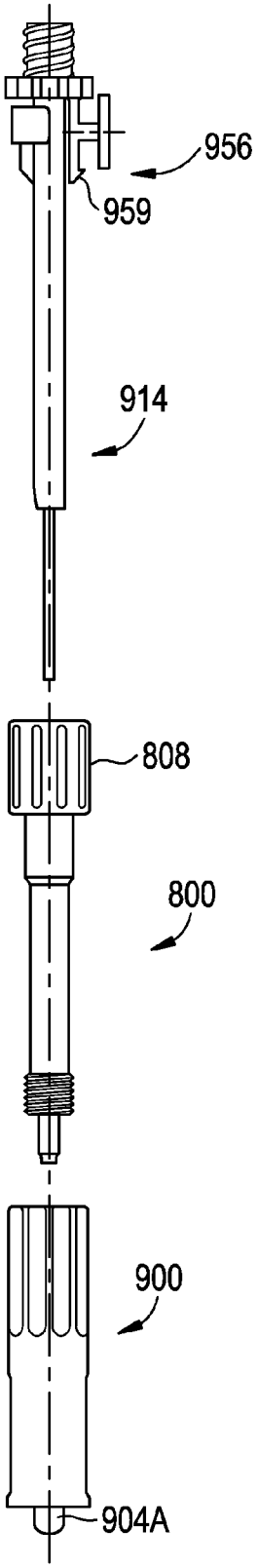
FIG. 21 is an exploded view of another exemplary system for delivering bone cement to a bone anchor, illustrating the anchor connection instrument, the cement delivery tube, and a counter-torque instrument of the system and a bone anchor.
Figure 22A:
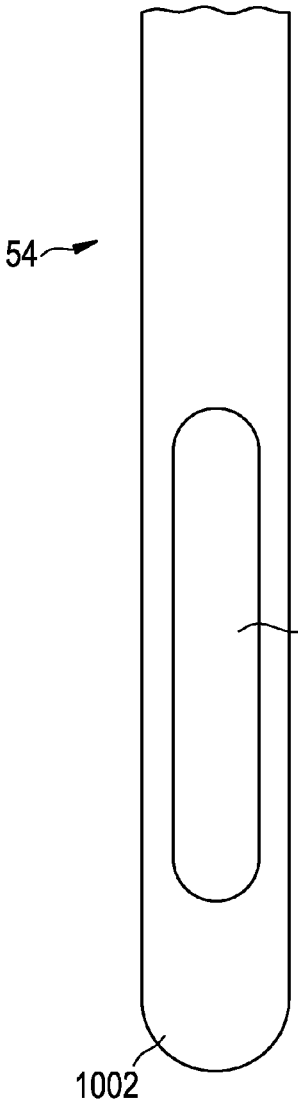
FIG. 22A is a front view of another exemplary embodiment of a cement delivery tube, illustrating the distal end of the tube.
Figure 22B:
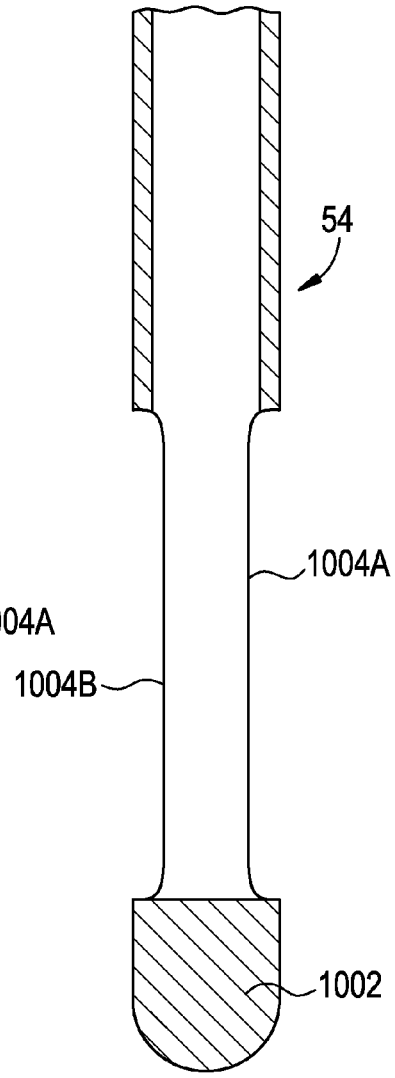
FIG. 22B is a side view in cross section of the distal end of the tube of FIG. 22A.
Figure 22C:
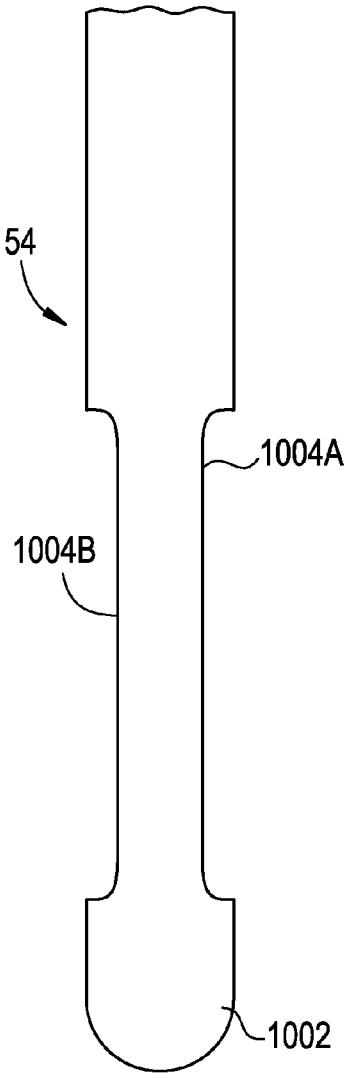
FIG. 22C is a side view of the distal end of the tube of FIG. 22A.

In open procedures, the length of the counter-torque instrument 900 and the anchor connection instrument 800 may be reduced, as illustrated in FIG. 21. FIG. 21 further illustrates another exemplary embodiment of a bone cement delivery tube 916 having a connection feature that permits the proximal end 956 of the tube 914 to be internally connected to the collar 808 of the anchor connection instrument 800. The connection feature, in the illustrated embodiment, includes one or more flexible, resilient prongs 959 that snap fit into a groove or opening in the inner wall of the collar 808. The distal end of the bone cement delivery tube may be configured to occlude a portion of the passage 34 in the bone anchor 16 to direct bone cement through selective openings 36 in the bone anchor 16. In one exemplary embodiment, the distal end of a bone cement delivery tube (e.g., tube 14, tube 614, tube 814, or tube 914) may be configured to occlude the distal end of the passage 34 thereby directing cement through only the openings 36 in the side wall of the bone engaging portion 32. The distal end 54 of the cement delivery tube 14 may include occlusion 1002 that prevents further cement flow and one or more slots or openings in the sidewall of the tube 14 that permit cement flow from the sidewalls rather than through a distal opening in the tube 14. In the exemplary embodiment, two diametrically opposed slots 1004A, 1004B are provided. The size, shape, and position of the slots may be varied depending on the desired cement flow.

Figure 23:
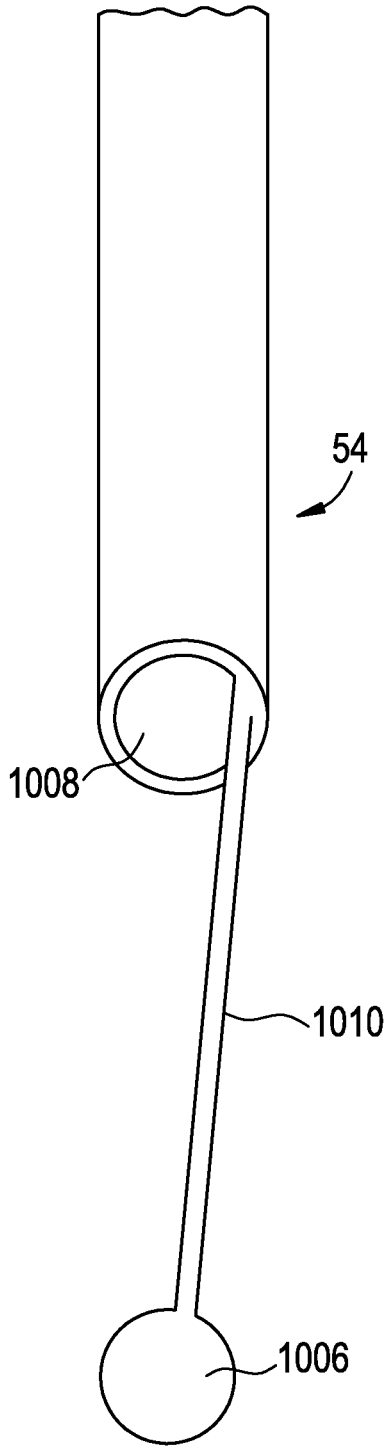
FIG. 23 is a perspective view of another exemplary embodiment of a cement delivery tube, illustrating the distal end of the tube.

In an alternative embodiment illustrated in FIG. 23, the distal end 54 of a bone cement delivery tube 14 may include an occlusion in the form of a plug 1006 spaced from the distal opening 1008 in the tube 14 by a wire or other reduced diameter structure *1010*. The plug 1006 may have any shape suitable to occlude the passage 34 in the bone anchor 16. The plug 1006, in the exemplary embodiment, is generally spherical in shape.

Figure 24A:
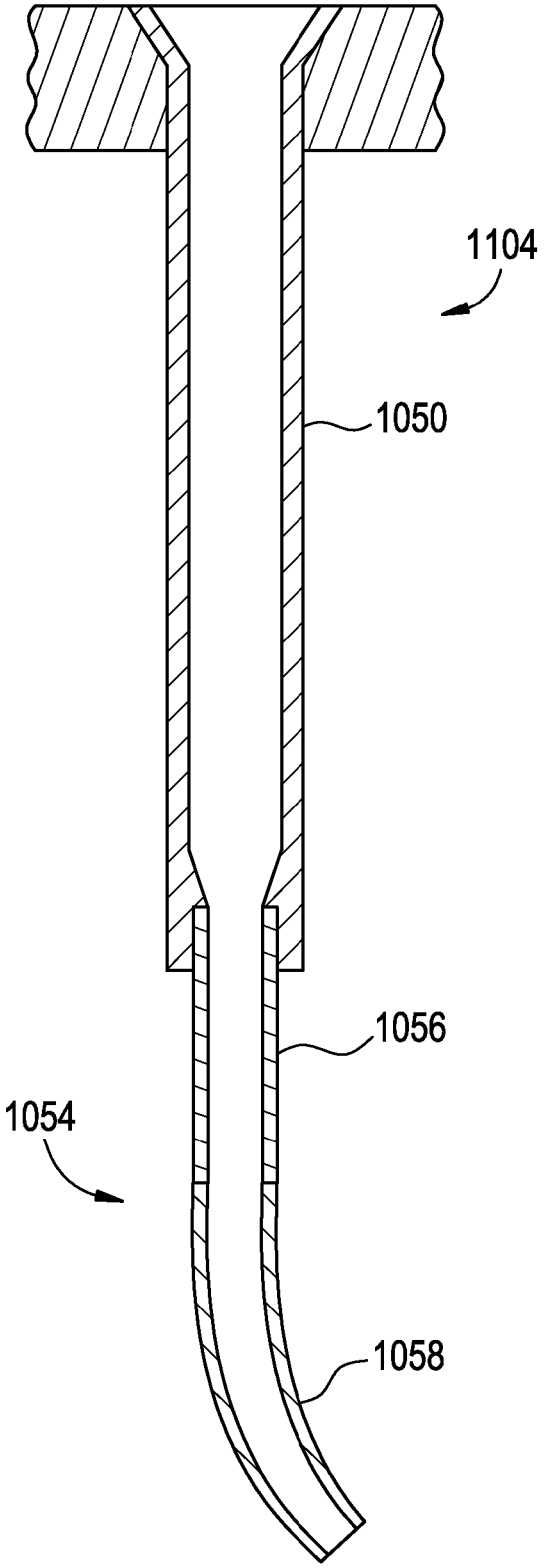
FIG. 24A is a side view in cross section of another exemplary embodiment of a cement delivery tube.
Figure 24B:
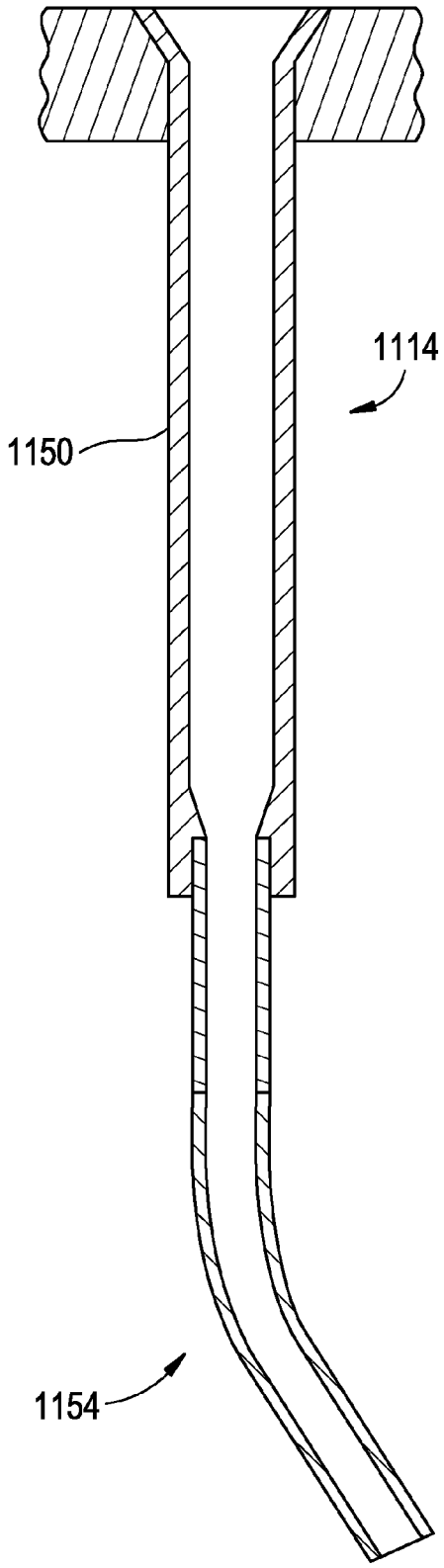
FIG. 24B is a side view in cross section of another exemplary embodiment of a cement delivery tube.

The distal end of a bone cement delivery tube may be flexible to facilitate placement of the tube in the passage 34 of the bone anchor 16. For example, the distal end 1054 of an exemplary cement delivery tube 1104 may include lengthwise sections of increased flexibility, as illustrated in FIG. 24A. The distal end 1054 of the exemplary tube 1104 includes a first lengthwise section 1056 and a second lengthwise section 1058 connected to and distal from the first section 1056. The first section 1056 may be constructed from a material having increased flexibility compared to the second section 1058 and compared to the proximal section 1050. For example, the first section 1056 may be constructed of a flexible polymer material, the second section 1058 may be constructed from a stiffer material, such as a metal (e.g., stainless steel), and the proximal section 1050 may be constructed of a stiffer material and/or have an increased wall thickness providing increased stiffness. Any number of lengthwise sections constructed from materials of differing flexibility may be provided. In an alternative embodiment of a bone cement delivery tube 1114, the continuous length of the distal end 1154 of the tube may be constructed from a flexible material while the proximal end 1150 of the tube 1114 may be constructed of from a stiffer material, such as a metal (e.g., stainless steel) and/or may have an increased wall thickness to provide increased stiffness.

While the systems and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

[1. A method of delivering cement to a spinal anchor anchored in a vertebra of a patient, the method comprising:

advancing a distal end of an anchor connection instrument through an opening in a proximal portion of a spinal anchor, the proximal portion of the spinal anchor having a slot for receiving a spinal rod and a thread for receiving a closure mechanism for securing the rod in the proximal portion, the distal end of the anchor connecting instrument including a first connection feature spaced apart from a second connection feature, the first connection feature comprising an external thread, the second connection feature comprising a drive tip located at a distal tip of the distal end of the anchor connection instrument, advancing the drive tip of the anchor connection instrument into a drive feature at a proximal opening in a passage formed in a distal bone engaging portion of the spinal anchor, the passage communicating with the opening in the proximal portion of the spinal anchor, rotating the first connection feature to engage the external thread of the first connection feature with the thread on the proximal portion of the spinal anchor, the first connection feature being positioned between the proximal end and the distal end of the anchor connection instrument a distance from the drive tip, the distance selected to allow the drive tip to be advanced into the drive feature of the distal bone engaging portion of the spinal anchor when the first connection feature engages the proximal portion of the spinal anchor, the anchor connection instrument holding the proximal portion of the spinal anchor relative to the distal bone engaging portion of the spinal anchor when the first connection feature engages the proximal portion of the spinal anchor and the second connection feature is advanced into the drive feature of the distal bone engaging portion of the spinal anchor, positioning a bone cement delivery tube through the anchor connection instrument, advancing a distal end of the bone cement delivery tube into the passage of the distal bone engaging portion of the spinal anchor, connecting a proximal end of the bone cement delivery tube to a bone cement delivery system, and injecting cement into the passage of distal bone engaging portion of the spinal anchor through the bone cement delivery tube.]

[2. The method of claim 1, wherein at least a portion the bone cement delivery system is positioned outside of a fluoroscopic imaging field about the patient.]

[3. The method of claim 1, further comprising removing the anchor connection instrument and the bone cement delivery tube from the spinal anchor, advancing a distal end of the anchor connection instrument through an opening in a proximal portion of a second spinal anchor, advancing the drive tip of the anchor connection instrument into a drive feature at a proximal opening in a passage formed in a distal bone engaging portion of the second spinal anchor, the passage communicating with the opening in the proximal portion of the second spinal anchor, rotating the first connection feature to engage the external thread of the first connection feature with the thread on the proximal portion of the second spinal anchor, positioning the bone cement delivery tube through the anchor connection instrument, advancing the distal end of the bone cement delivery tube into the passage of the distal bone engaging portion of the second spinal anchor, and injecting cement into the passage of distal bone engaging portion of second the spinal anchor through the bone cement delivery tube.]

[4. The method of claim 1, wherein the thread of the first connection feature is interrupted at two spaced apart, opposed unthreaded sections and further comprising inserting the first connection feature into the proximal portion of the bone anchor with the unthread sections facing the thread, and rotating the first connection feature to engage the thread on the first connection feature with the thread on the proximal portion of the bone anchor.]

[5. The method of claim 1, further comprising connecting a spinal rod to the proximal portion of the bone anchor after injecting cement into spinal anchor.]

[6. The method of claim 5, further comprising connecting a connection mechanism to the proximal end of the bone anchor to capture to the spinal rod to the spinal anchor.]

*7. A method of delivering cement to a spinal anchor anchored in a vertebra of a patient, the method comprising:*

*advancing a distal end of an anchor connection instrument into a proximal portion of a spinal anchor, the proximal portion of the spinal anchor having a slot for receiving a spinal rod and a thread for receiving a closure mechanism for securing the rod in the proximal portion, the distal end of the anchor connection instrument including a first connection feature spaced apart from a second connection feature, the first connection feature comprising an external thread, the second connection feature comprising a distal tip of the distal end of the anchor connection instrument,*

*advancing the distal tip of the anchor connection instrument into a proximal opening in a passage formed in a distal bone engaging portion of the spinal anchor, the passage communicating with the proximal portion of the spinal anchor,*

*rotating the first connection feature to engage the external thread of the first connection feature with the thread on the proximal portion of the spinal anchor, the first connection feature being positioned between the proximal end and the distal end of the anchor connection instrument a distance from the distal tip, the distance selected to allow the distal tip to be advanced into the proximal opening of the distal bone engaging portion of the spinal anchor when the first connection feature engages the proximal portion of the spinal anchor, the anchor connection instrument holding the proximal portion of the spinal anchor relative to the distal bone engaging portion of the spinal anchor when the first connection feature engages the proximal portion of the spinal anchor and the second connection feature is advanced into the proximal opening of the distal bone engaging portion of the spinal anchor,*

*positioning a bone cement delivery tube through the anchor connection instrument, and*

*injecting cement into the passage of the distal bone engaging portion of the spinal anchor through the bone cement delivery tube,*

*wherein the first connection feature and the second connection feature are advanced simultaneously,*

*wherein the bone cement delivery tube includes a handle comprising two wings extending laterally-outward from a proximal end of the bone cement delivery tube, and a connector disposed between the two wings of the handle for connecting the bone cement delivery tube to a reservoir of bone cement.*

*8. The method of claim 7, further comprising removing the anchor connection instrument after injecting cement into the passage of the distal bone engaging portion of the spinal anchor.*

*9. The method of claim 7, wherein removing the anchor connection instrument includes rotating the first connection feature to disengage the external thread of the first connection feature from the thread of the proximal portion of the bone anchor.*

*10. The method of claim 7, further comprising positioning the anchor connection instrument through a tubular extension.*

*11. The method of claim 10, wherein the tubular extension is connected to the bone anchor.*

*12. The method of claim 7, further comprising connecting a spinal rod to the proximal portion of the spinal anchor after injecting cement into the spinal anchor.*

*13. The method of claim 12, further comprising connecting a closure mechanism to the proximal end of the spinal anchor to capture the spinal rod to the spinal anchor.*

*14. The method of claim 7, wherein the anchor connection instrument comprises a tubular instrument body having a protruding annular portion at a proximal end thereof.*

*15. The method of claim 7, further comprising connecting the bone cement delivery tube to a reservoir of bone cement and applying pressure to bone cement in the reservoir to move the bone cement into the bone cement delivery tube.*

*16. The method of claim 7, further comprising injecting the cement through openings in a sidewall of the distal bone engaging portion of the spinal anchor and into surrounding bone.*

*17. A method of delivering cement to a spinal anchor anchored in a vertebra of a patient, the method comprising:*

*advancing a distal end of an anchor connection instrument into a proximal portion of a spinal anchor, the proximal portion of the spinal anchor having a slot for receiving a spinal rod and a thread for receiving a closure mechanism for securing the rod in the proximal portion, the distal end of the anchor connection instrument including a first connection feature spaced apart from a second connection feature, the first connection feature comprising an external thread, the second connection feature comprising a distal tip of the distal end of the anchor connection instrument,*

*advancing the distal tip of the anchor connection instrument into a proximal opening in a passage formed in a distal bone engaging portion of the spinal anchor, the passage communicating with the proximal portion of the spinal anchor,*

*rotating the anchor connection instrument to engage the external thread of the first connection feature with the thread on the proximal portion of the spinal anchor, the first connection feature being positioned between the proximal end and the distal end of the anchor connection instrument a distance from the distal tip, the distance selected to allow the distal tip to be advanced into the proximal opening of the distal bone engaging portion of the spinal anchor as the anchor connection instrument is rotated, the anchor connection instrument holding the proximal portion of the spinal anchor relative to the distal bone engaging portion of the spinal anchor when the first connection feature engages the proximal portion of the spinal anchor and the second connection feature is advanced into the proximal opening of the distal bone engaging portion of the spinal anchor*

*positioning a bone cement delivery tube through the anchor connection instrument,*

*placing a distal end of the bone cement delivery tube into fluid communication with the passage of the distal bone engaging portion of the spinal anchor,*

*coupling a proximal end of the bone cement delivery tube to the proximal end of the anchor connection instrument, and*

*injecting cement into the passage of the distal bone engaging portion of the spinal anchor through the bone cement delivery tube,*

*wherein rotating the first connection feature simultaneously rotates the second connection feature,*

*wherein the bone cement delivery tube includes a handle comprising two wings extending laterally-outward*

*from the proximal end of the bone cement delivery tube, and a connector disposed between the two wings of the handle for connecting the bone cement delivery tube to a reservoir of bone cement.*

*18. The method of claim 17, further comprising removing the anchor connection instrument after injecting cement into the passage of the distal bone engaging portion of the spinal anchor.*

*19. The method of claim 18, wherein removing the anchor connection instrument includes rotating the anchor connection instrument to disengage the external thread of the first connection feature from the thread of the proximal portion of the bone anchor.*

*20. The method of claim 17, further comprising positioning the anchor connection instrument through a tubular extension.*

*21. The method of claim 20, wherein the tubular extension is connected to the bone anchor.*

*22. The method of claim 17, further comprising connecting a spinal rod to the proximal portion of the spinal anchor after injecting cement into the spinal anchor.*

*23. The method of claim 22, further comprising connecting a closure mechanism to the proximal end of the spinal anchor to capture the spinal rod to the spinal anchor.*

*24. The method of claim 17, wherein the anchor connection instrument comprises a tubular instrument body having a protruding annular portion at a proximal end thereof.*

*25. The method of claim 17, wherein the bone cement delivery tube includes a proximal connector for connecting the bone cement delivery tube to a cement delivery system.*

*26. The method of claim 17, further comprising connecting the bone cement delivery tube to a reservoir of bone cement and applying pressure to bone cement in the reservoir to move the bone cement into the bone cement delivery tube.*

*27. The method of claim 17, further comprising injecting the cement through openings in a sidewall of the distal bone engaging portion of the spinal anchor and into surrounding bone.*

* * * * *